United States Patent
Toyonaga et al.

(10) Patent No.: US 11,937,977 B2
(45) Date of Patent: Mar. 26, 2024

(54) COMPOUNDING AND NON-RIGID IMAGE REGISTRATION FOR ULTRASOUND SPECKLE REDUCTION

(71) Applicant: The Board of Trustees of the Leland Stanford Junior University, Stanford, CA (US)

(72) Inventors: Noah Yuzo Toyonaga, Stanford, CA (US); Yilei Li, Stanford, CA (US); Steven Chu, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 623 days.

(21) Appl. No.: 17/254,014

(22) PCT Filed: Jun. 18, 2019

(86) PCT No.: PCT/US2019/037771
§ 371 (c)(1),
(2) Date: Dec. 18, 2020

(87) PCT Pub. No.: WO2019/246127
PCT Pub. Date: Dec. 26, 2019

(65) Prior Publication Data
US 2021/0219961 A1    Jul. 22, 2021

Related U.S. Application Data

(60) Provisional application No. 62/687,138, filed on Jun. 19, 2018.

(51) Int. Cl.
*A61B 8/00* (2006.01)
*A61B 8/08* (2006.01)
(Continued)

(52) U.S. Cl.
CPC .......... *A61B 8/4245* (2013.01); *A61B 8/5253* (2013.01); *A61B 8/5269* (2013.01);
(Continued)

(58) Field of Classification Search
CPC ... A61B 8/4245; A61B 8/5253; A61B 8/5269; A61B 8/4488; A61B 8/5246; A61B 8/14;
(Continued)

(56) References Cited

U.S. PATENT DOCUMENTS 6,524,252 B1 * 2/2003 Yu .................... G01S 7/52074
600/443
2004/0054284 A1  3/2004 Cai et al.
(Continued)

FOREIGN PATENT DOCUMENTS

WO    0247533 A2    6/2002

OTHER PUBLICATIONS

Krücker, J.F., Meyer, C.R., LeCarpentier, G.L., Fowlkes, J.B. and Carson, P.L., 2000. 3D spatial compounding of ultrasound images using image-based nonrigid registration. Ultrasound in medicine & biology, 26(9), pp. 1475-1488.*
(Continued)

*Primary Examiner* — Zhitong Chen
(74) *Attorney, Agent, or Firm* — Kilpatrick Townsend & Stockton LLP

(57) ABSTRACT

This disclosure relates to ultrasound imaging with reduced speckle. Ultrasound imaging with frequency compounding and angle compounding is disclosed. Techniques are disclosed to make ultrasound imaging with frequency and angle compounding more robust. One such technique is non-rigid image registration to align ultrasound images for angle compounding. Another disclosed technique includes selecting a subset of ultrasound images for non-rigid ultrasound image registration.

21 Claims, 19 Drawing Sheets

(51) Int. Cl.
  *G01S 15/89* (2006.01)
  *G06T 5/00* (2006.01)
  *G06T 7/20* (2017.01)
  *G06T 7/32* (2017.01)
  *G06T 7/37* (2017.01)
(52) U.S. Cl.
  CPC ........ *G01S 15/895* (2013.01); *G01S 15/8995* (2013.01); *G06T 5/005* (2013.01); *G06T 7/20* (2013.01); *G06T 7/32* (2017.01); *G06T 7/37* (2017.01); *G06T 2207/10132* (2013.01)
(58) Field of Classification Search
  CPC ..... A61B 8/145; A61B 8/4461; G01S 15/895; G01S 15/8995; G06T 5/005; G06T 7/20; G06T 7/32; G06T 7/37; G06T 2207/10132
  See application file for complete search history.

(56) References Cited

U.S. PATENT DOCUMENTS

| | | | |
|---|---|---|---|
| 2005/0101865 A1* | 5/2005 | Hao | G01S 7/52038 600/447 |
| 2008/0194958 A1 | 8/2008 | Lee et al. | |
| 2008/0208061 A1 | 8/2008 | Halmann | |
| 2013/0294665 A1* | 11/2013 | Rao | G01S 15/8995 382/131 |
| 2014/0066768 A1 | 3/2014 | Sui et al. | |
| 2016/0282467 A1 | 9/2016 | Olsson | |

OTHER PUBLICATIONS

Tran, D., Hor, K.W., Kamani, A., Lessoway, V. and Rohling, R.N., 2008, March. Adaptive spatial compounding for improving ultrasound images of the epidural space on human subjects. In Medical Imaging 2008: Ultrasonic Imaging and Signal Processing (vol. 6920, pp. 157-168). SPIE.*

Lin et al., "A Motion Compounding Technique for Speckle Reduction in Ultrasound," Journal of Digital Imaging, vol. 23, No. 3, Jun. 2010, pp. 246-257.

Application No. PCT/US2019/037771, International Preliminary Report on Patentability, dated Dec. 30, 2020, 9 pages.

Application No. PCT/US2019/037771, International Search Report and Written Opinion, dated Sep. 9, 2019, 10 pages.

Tran et al., "Adaptive Spatial Compounding for Improving Ultrasound Images of the Epidural Space," Medical Imaging 2007: Ultrasonic Imaging and Signal Processing Proceedings of SPIE, vol. 6513, 65130W, Mar. 12, 2007, 12 pages.

Application No. EP19822811.6, Extended European Search Report, dated Jan. 14, 2022, 8 pages.

* cited by examiner

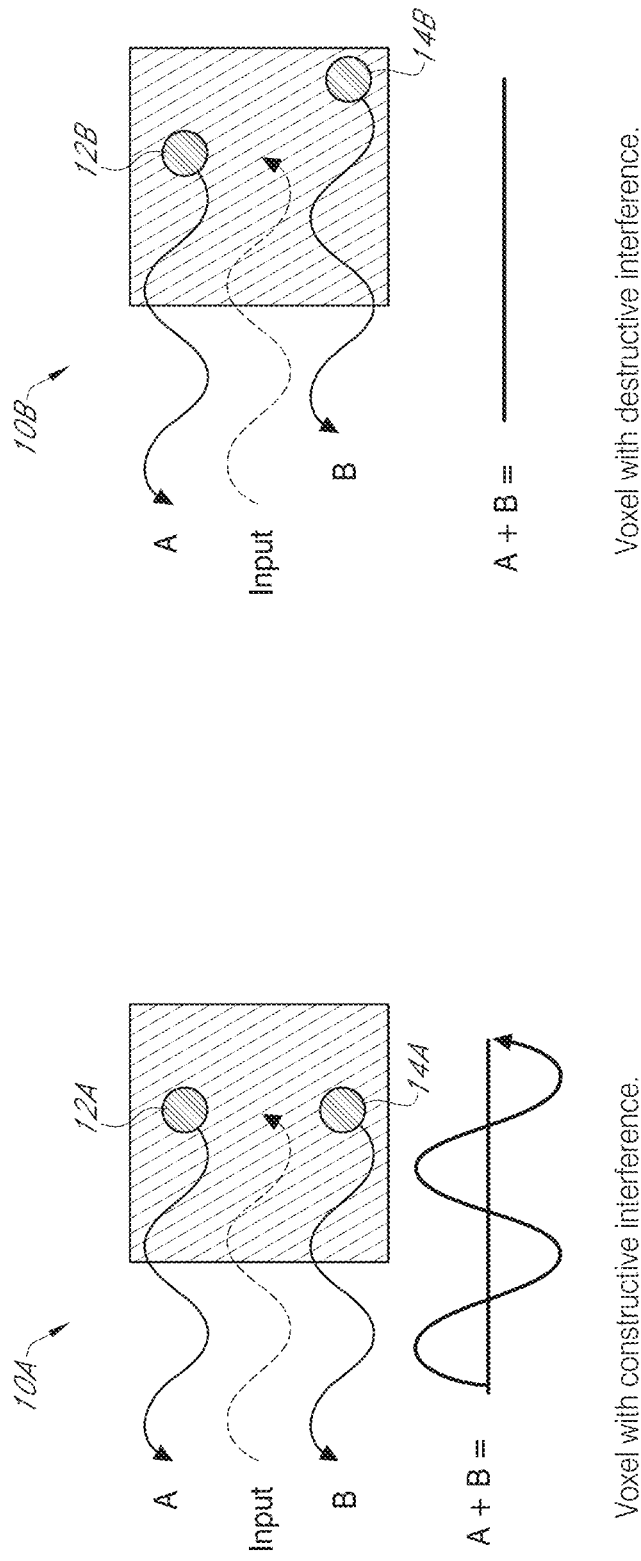

Operator-induced:
The imaging volume is distorted by pressure from the US probe.

Patient motion:
The imaging volume may change between images due to breathing, heart beat, etc.

Index of Refraction:
The varying index of refraction in the imaging volume gives rise to weak lensing of the sound pulses.

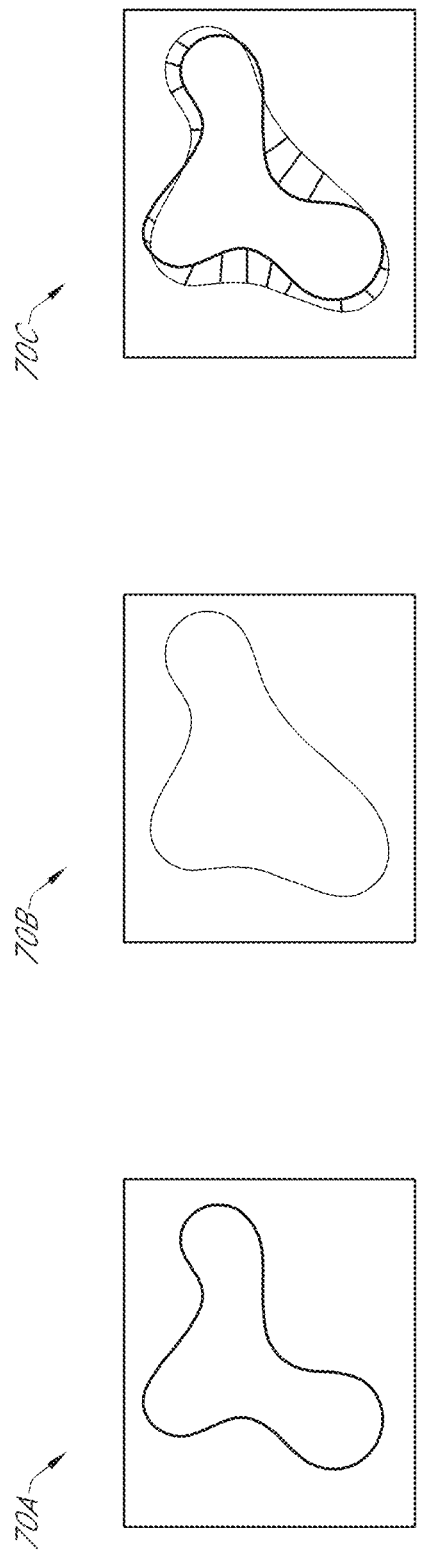

COMPOUNDING AND NON-RIGID IMAGE REGISTRATION FOR ULTRASOUND SPECKLE REDUCTION

RELATED APPLICATION

This application claims the benefit of priority of U.S. Provisional Patent Application No. 62/687,138, filed Jun. 19, 2018, titled "NON-RIGID IMAGE REGISTRATION AND PHASE FRONT MODULATION FOR ULTRASOUND SPECKLE REDUCTION," the disclosure of which is hereby incorporated by reference herein in its entirety for all purposes.

BACKGROUND

Technological Field

The disclosed technology relates to ultrasound imaging.

Description of the Related Technology

Ultrasound is becoming an increasingly important tool for diagnostic imaging with many desirable characteristics. Ultrasound is relatively fast, real-time imaging, at low cost, and without exposure to ionizing radiation. In addition, refinements such as color Doppler, shear wave and contrast agent labeling offer valuable additional diagnostic information that complements x-ray, computed tomography (CT) and magnetic resonance imaging (MRI) imaging modalities. However, conventional ultrasound imaging suffers from the presence of significant speckle noise. Useful resolution of ultrasound imaging in clinical practice can be degraded.

SUMMARY OF CERTAIN ASPECTS

The innovations described in the claims each have several aspects, no single one of which is solely responsible for its desirable attributes. Without limiting the scope of the claims, some prominent features of this disclosure will now be briefly described.

One aspect of this disclosure is a method of generating a compounded ultrasound image with reduced speckle. The method comprises generating ultrasound image data using an ultrasound probe; frequency compounding the ultrasound image data to generate frequency compounded ultrasound image data; non-rigidly registering ultrasound images from the frequency compounded ultrasound image data to generate registered ultrasound images; angle compounding the registered ultrasound images to generate a compounded ultrasound image; and outputting the compounded ultrasound image.

The method can include selecting a subset of images of the frequency compounded ultrasound image data for the non-rigidly registering, in which the subset of images comprises the ultrasound images from the frequency compounded ultrasound image data. A second image of the subset can be selected based on an angular displacement relative to a first image of the subset satisfying a threshold. The selecting and the non-rigidly registering can be performed in an amount of time that is no greater than a frame rate of the ultrasound probe. The selecting and the non-rigidly registering can be performed as post processing operations. The selecting can include performing a cross correlation between of images of the frequency compounded ultrasound image data.

The non-rigidly registering can comprise determining a transformation to elastically distort a second image of the frequency compounded images to a first image of the frequency compounded images, wherein the first image and the second image correspond to a region of interest imaged from different angles; and applying the transformation to the second image.

The non-rigidly distorting can comprise applying an iterative gradient-based algorithm of determining a displacement vector to transform a second image of the frequency compounded images to align with a first image of the frequency compounded images.

The method can further comprise transmitting an ultrasound pulse, by the ultrasound probe, with pulse shaping to compensate for a frequency response of one or more ultrasound transducers of the ultrasound probe; and generating the ultrasound image data based on at least one echo of the ultrasound pulse received by the ultrasound probe.

The method can further comprise performing fast Fourier decomposition of echo data from the ultrasound probe to generate the ultrasound image data for the frequency compounding.

The method can further comprise tracking a region of interest of an object being imaged by the ultrasound probe. The method can additionally comprise determining a displacement of the ultrasound probe based on the tracking; and controlling beam steering of the ultrasound probe based on the determining.

Another aspect of this disclosure is an ultrasound imaging system for generating ultrasound images with reduced speckle. The ultrasound imaging system comprises an ultrasound probe configured to generate ultrasound imaging data and one or more computing devices in communication with the ultrasound probe. The one or more computing devices are configured to: frequency compound the ultrasound image data from the ultrasound probe to generate frequency compounded ultrasound image data; non-rigidly register ultrasound images from the frequency compounded ultrasound image data to generate registered ultrasound images; and angle compound the registered ultrasound images to generate a compounded ultrasound image; and output the compounded ultrasound image.

The one or more computing devices can select a subset of images of the frequency compounded ultrasound image data based on an angular displacement satisfying a threshold, in which the subset of images comprises the ultrasound images from the frequency compounded ultrasound image data.

The one or more computing devices can non-rigidly register by at least applying an iterative gradient-based algorithm of determining a displacement vector to transform a second image of the frequency compounded images to align with a first image of the frequency compounded images.

The ultrasound imaging system can to transmit an ultrasound pulse from the ultrasound probe with pulse shaping to compensate for a frequency response of one or more ultrasound transducers of the ultrasound probe.

The one or more computing devices can perform Fourier decomposition of the ultrasound image data prior to frequency compounding the ultrasound image data.

The ultrasound probe can comprise a phased array of transducers, and the one or more computing devices can track a region of interest of an object being imaged by the ultrasound probe, determine a displacement of the ultrasound probe based on tracking the region of interest, and control beam steering of the ultrasound array based on the determined displacement.

The ultrasound imaging system can further comprise a display in communication with the one or more computing devices, in which the display is configured to visually present the compounded ultrasound image.

Another aspect of this disclosure is non-transitory computer-readable storage comprising memory storing computer executable instructions, wherein the computer-executable instructions, when executed by one or more computing devices, cause a method to be performed, the method comprising: frequency compounding ultrasound image data to generate frequency compounded ultrasound image data; non-rigidly registering ultrasound images from the frequency compounded ultrasound image data to generate registered ultrasound images; angle compounding the registered ultrasound images to generate a compounded ultrasound image; and outputting the compounded ultrasound image.

Another aspect of this disclosure is a method of generating an ultrasound image with reduced speckle. The method comprises: frequency compounding ultrasound image data from an ultrasound probe to generate frequency compounded ultrasound image data; tracking a region of interest being imaged between frames of the frequency compounded ultrasound image data to determine a spatial location of the region of interest; computing a probe displacement of the ultrasound probe based on the determined spatial location of the region of interest; controlling a phased array of the ultrasound probe to steer an ultrasound beam to the region of interest based on the computed probe displacement; selecting an ultrasound image from the frequency compounded ultrasound image data based on angular displacement associated with the ultrasound image satisfying a threshold; registering and angle compounding the selected ultrasound image with one or more other selected ultrasound images to generate a compounded ultrasound image; and outputting the compounded ultrasound image.

For purposes of summarizing the disclosure, certain aspects, advantages and novel features of the innovations have been described herein. It is to be understood that not necessarily all such advantages may be achieved in accordance with any particular embodiment. Thus, the innovations may be embodied or carried out in a manner that achieves or optimizes one advantage or group of advantages as taught herein without necessarily achieving other advantages as may be taught or suggested herein.

BRIEF DESCRIPTION OF THE DRAWINGS

Embodiments of this disclosure will now be described, by way of non-limiting examples, with reference to the accompanying drawings.

FIGS. 1A to 1D illustrate various types of interference from scatterers in a voxel. FIG. 1A illustrates a voxel with constructive interference from scatterers. FIG. 1B illustrates a voxel with destructive interference from scatterers. FIG. 1C the voxel of FIG. 1B probed from a different angle. FIG. 1D the voxel of FIG. 1B probed with a different frequency.

FIG. 2A illustrates an operator-induced distortion of an ROI. FIG. 2B illustrates a patient-induced distortion of an ROI. FIG. 2C illustrates distortion of an ROI induced by a varying index of refraction.

FIG. 3A illustrates imaging an ROI from 0 degrees. FIG. 3B illustrates imaging the ROI of FIG. 3A and distorting tissue. FIG. 3C illustrates the ROI of FIG. 3A being inaccessible for imaging.

FIG. 4A illustrates imaging an ROI from 0 degrees. FIG. 4B illustrates imaging the ROI of FIG. 4A from 20 degrees with manual rotation of an ultrasound probe. FIG. 4C illustrates imaging the ROI of FIG. 4A from 20 degrees with beam steering.

FIGS. 6A to 6C illustrate non-rigid image registration. FIG. 6A illustrates a first image. FIG. 6B illustrates a second image. FIG. 6C illustrate non-rigid registration of the second image to the first image.

DETAILED DESCRIPTION OF CERTAIN EMBODIMENTS

Figure 1D:
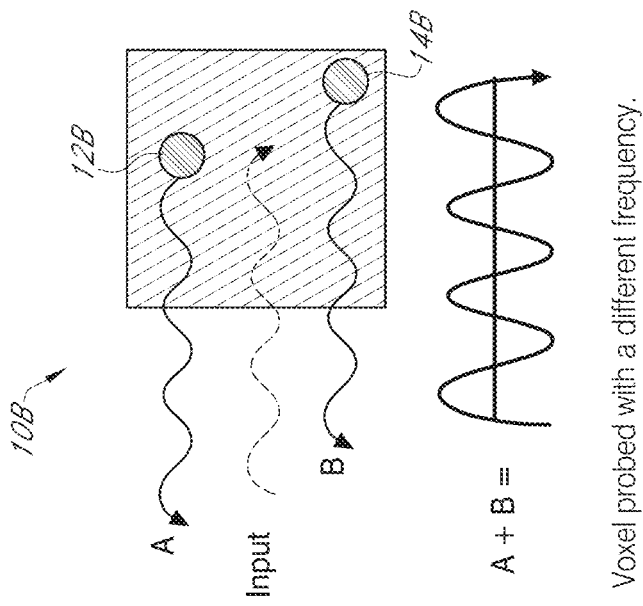

The following detailed description of certain embodiments presents various descriptions of specific embodiments. However, the innovations described herein can be embodied in a multitude of different ways, for example, as defined and covered by the claims. In this description, reference is made to the drawings where like reference numerals can indicate identical or functionally similar elements. It will be understood that elements illustrated in the figures are not necessarily drawn to scale. Moreover, it will be understood that certain embodiments can include more elements than illustrated in a drawing and/or a subset of the elements illustrated in a drawing. Further, some embodiments can incorporate any suitable combination of features from two or more drawings. The headings provided herein are for convenience only and do not necessarily affect the scope or meaning of the claims.

Ultrasounds are sound waves with frequencies above the audible range of humans. Ultrasound frequencies are typically in a range above 20 kilohertz (kHz) up to several gigahertz (GHz). As discussed above, ultrasound imaging can suffer from the presence of significant speckle noise, which can degrade the useful resolution of ultrasound imaging in clinical practice. The present disclosure provides techniques for frequency compounding and spatial compounding (also known as angle compounding) to reduce speckle in ultrasound imaging.

Methods disclosed herein combine angle and frequency compounding for ultrasound imaging. Techniques are provided for making these methods robust to distortions that are related to angle and frequency compounding. Such techniques include non-rigid image registration, identifying and selecting a subset of ultrasound images for non-rigid image registration, and frequency compensation.

Non-rigid image registration techniques are disclosed that can improve speckle reduction. By performing non-rigid image registration and then spatially compounding the registered images, improved and/or maximum speckle reduction can be achieved. Non-rigid image registration can compensate for spatial distortions.

A set of ultrasound images for spatial compounding can be identified and selected from a larger set of ultrasound images. While the set of all ultrasound images captured during an ultrasound scan could be used for registration and spatial compounding, identifying and selecting a set of the ultrasound images can significantly decrease the amount of computation and time to perform spatial compounding to generate a compounded ultrasound image. Identifying and selecting a set of ultrasound images for spatial compounding can decrease the likelihood of incorrect registrations (e.g., creating artifacts induced by errors in the image registration process).

In an illustrative example, an ultrasound probe can operate at a rate of 10 to 100 frames per second. A scan of tissue might take several seconds to ensure proper alignment. However, only about 10 to 20 of the captured ultrasound images located at suitable displaced angles may contribute to speckle reduction achieved by spatial compounding. By properly selecting (or culling) a selected set of ultrasound images for alignment and spatial compounding, the speed of generating a compounded ultrasound image with reduced speckle can be increased and/or the change of incorrect registrations can be reduced.

Frequency compensation techniques are also disclosed herein. This can allow board band frequency compounding to be performed, which can increase and/or maximize speckle reduction. Frequency compensation can compensate for a non-ideal frequency response of one or more ultrasound transducers of an ultrasound probe.

In certain applications, beam steering can be performed using a phase array control. Beam steering can be combined with region of interest (ROI) tracking to capture a similar or the same spatial region throughout an ultrasound sweep. Alternatively, the phased array can be used to capture a full sweep of ultrasound images in an ultrasound scan, including points outside of the direction of the ROI. This can result in a large data set that can be culled in post processing to include a reasonable number of images with overlap in the ROI. From either approach with the phased array, a set of overlapping ultrasound images can be registered in a non-rigid registration scheme. There is a tradeoff between (a) processing in real time in approaches that involve ROI tracking and (b) data capture rate and storage size in post processing approaches.

Non-rigid image registration techniques disclosed herein be implemented with one or more other techniques to generate an ultrasound image with reduced speckle. For example, in an embodiment, a real time non-rigid monomodal (e.g., ultrasound only) image registration framework, real time region of interest (ROI) tracking for control of a beam steering apparatus, and fast Fourier analysis are combined in an ultrasound imaging system.

Disclosed systems can improve diagnostic ultrasound with angle and frequency compounding methods. Standard diagnostic ultrasound hardware can be used with the angle and frequency compounding methods disclosed herein. Disclosed systems are robust to distortions in the imaged tissue (e.g., due to patient breathing, pulse, pressure from the ultrasound probe, other sources, or any combination thereof), are robust to distortions in ultrasound images due to variation in tissue indices of refractions, and are robust to the surface geometry of the imaged structure.

A system that aligns a set of ultrasound images with non-rigid registration parameters for achieving speckle reduction is disclosed herein. The system can compensate for non-rigid variations in image geometry due to distortions. Such distortions can be caused by the ultrasound probe, breathing, heartbeat, and/or other sources. The system can use multiple images to correct distortions in ultrasound images due to weak lensing caused by index of refraction variations in volumes comparable or larger than the wavelengths of sound. The system can reduce speckle noise by compounding images taken at different angles. The system can use digital pulse shaping to compensate for the frequency response of the ultrasound device. The system can reduce speckle due to frequency compounding allowed by the fast Fourier decomposition of the echo signal into separated frequency components. The system can continuously approximate image registration parameters from incoming stream of ultrasound device. The system can automatically select a set of images from a stream of images by selecting images whose geometric properties will lead to improved (e.g., optimum) speckle reduction once registered and compounded. The system can perform selection of images and group registration in real time in certain instances. The system can use hardware acceleration to reduce computation time.

As disclosed herein, beam steering can track an ROI for the purpose of speckle reduction. In certain embodiments, beam steering can be combed with ROI tracking for purposes of imaging the ROI. Embodiments discussed herein relate to image registration that can compensate for non-rigid distortions in real time. Techniques that involve compounding images that overlap on a ROI are also disclosed.

Speckle Noise

Speckle noise can arise from the non-uniform distribution of sub-wavelength scatterers inside an imaging voxel. FIGS. 1A to 1D illustrate various ways scatters in a voxel being imaged can result in interference. A voxel can be a volumetric pixel. FIGS. 1A to 1D illustrate different interference in a voxel. An input beam or incident beam is applied to each of the illustrated voxels and interference is reflected from scatters of each of the voxels.

FIGS. 1A and 1B illustrate how a distribution of scatters in a voxel can lead to constructive or destructive interference. FIG. 1A illustrates a voxel 10A that includes scatters 12A and 14A that can cause constructive interference with an input beam applied. FIG. 1B illustrates a voxel 10B that includes scatters 12B and 14B that can cause destructive interference with the input beam applied. The difference between the voxels 10A and 10B is the position of scatterers 12A and 14A in the voxel 10A compared to the position of the scatterers 12B and 14B in the voxel 10B.

Figure 1C:
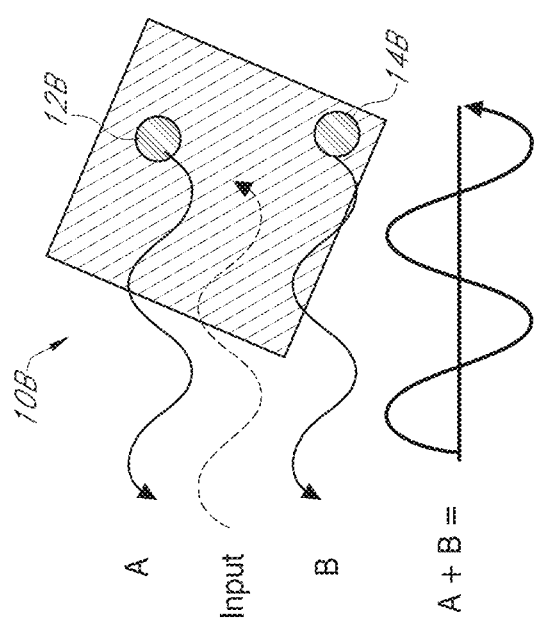

FIG. 1C illustrates the voxel 10B of FIG. 1B probed from a different angle. As shown in FIG. 1C, backscattered interference from an ultrasound voxel is affected by the incident beam angle because the scatters 12B and 14B have changed position relative to the incident beam compared to in FIG. 1B. FIGS. 1B and 1C illustrate the effect of changing the angle of incidence of a probing beam.

FIG. 1D illustrates the voxel 10B of FIG. 1B probed with a different frequency. As shown in FIG. 1D, the interference from a set of scatterers 12B and 14B can depend on the probing frequency because the interference can be determined by the displacement of the scatterers 12B and 14B relative to the phase of the incident beam. When the frequency of the beam is changed, the same scattering objects will have different displacements relative to the new phase. FIGS. 1B and 1D illustrate the effect of changing the probing frequency.

Ultrasound images formed from different frequency bands in a single RF signal can be compounded to reduce speckle noise. In at least some embodiments, speckle reduction can be achieved by compounding images made with Gaussian-shaped pulses designed to achieve a minimal or lowered product of frequency bandwidth and time duration.

By using frequency and angular compounding methods together and/or simultaneously, speckle can be reduced further than by using either technique alone. In at least some embodiments, combining frequency and angle compounding reduces speckle noise multiplicatively. If $S_A$, $S_F$, and $S_C$ are the speckle reduction factors corresponding to angle, frequency, and the combined compounding methods, respectively, then:

$$S_C = S_A \times S_F \qquad (1)$$

As an example, a total reduction ($S_C$) of at least 10 times should be possible.

Sources of Distortion in Imaging Volumes

The shape of a region of interest (ROI) may change in the course of generating a set of images (such as a set of images used for angular compounding). Variations in the shape of the ROI can reduce the effective resolution of the compounded image because features may not be correctly aligned across the set of images. This misalignment appears as blurring in the compounded image. By correcting for these variations in structure, resolution in the compounded image can be maintained.

Figure 2A:
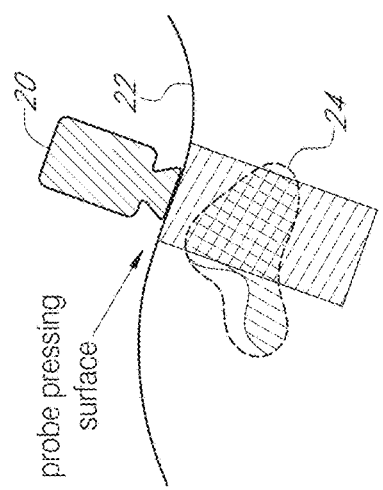
FIGS. 2A to 2C illustrate various distortions of a region of interest (ROI) being imaged.
Figure 2B:
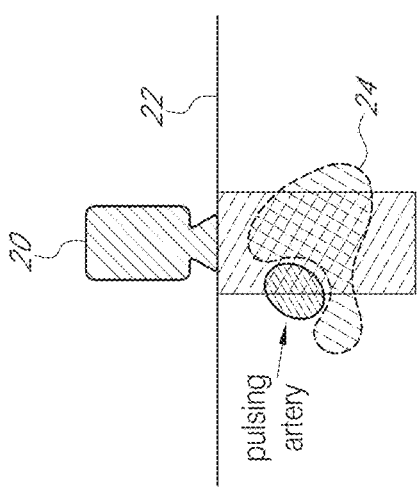
Figure 2C:
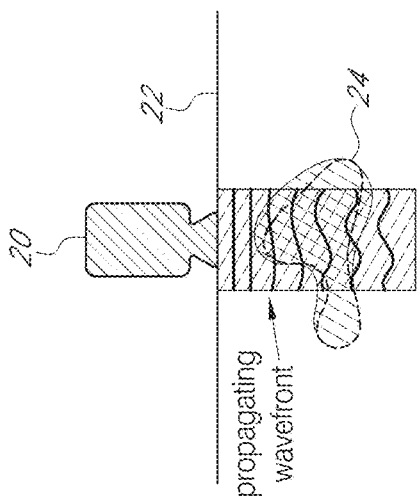

Distortions in the shape of an ROI may be induced by the contact force of an ultrasound probe, motion of a patient such as breathing, from refraction of the sound waves due to variations in the index of refraction of different tissue material, from other factors, or any suitable combination thereof. FIGS. 2A to 2C illustrate various source of distortion of an ROI. Such distortions and/or others can be compensated for by image registration techniques disclosed herein. In FIGS. 2A to 2C, a shaded shadow indicates a 'true' shape of the ROI and dotted lines indicate the distorted image observed in an ultrasound image.

In FIG. 2A, an ultrasound probe 20 in contact with a surface 22 of an object being imaged is imaging an imaging volume 24. The surface 22 can be skin of a person. The imaging volume 24 can be below the skin of a person. The imaging volume 24 can be referred to as an ROI. As shown in FIG. 2A, an operator may cause non-rigid geometric changes in an imaged volume during image acquisition. Such changes may be referred to as operator-induced variations. This may be a result from the pressure used to ensure good contact between the surface 22 and ultrasound probe 20. As the ultrasound probe 20 is moved to different imaging locations, the pressure can shift the imaged volume into different configurations.

As shown in FIG. 2B, the imaging volume 24 may also have geometric variation due to other changing conditions such as breathing, muscle contractions, heart beat and other motions of the patient. Such changes may be referred to as patient-induced variations. Algorithms disclosed herein can construct more precise images through the elastic image corrections described herein. In addition, because of the rapid image acquisition time of ultrasound, images can be sorted with respect to different parts of the breathing and heart-beat cycles for additional clinical information. For instance, a sequence of images taken at different times of the breathing cycle can be used to observe localized changes in lung expansion. Similarly, a series of images of arteries taken over a heart-beat cycle can be used to monitor the elasticity of specific portions of an artery.

As shown in FIG. 2C, an ultrasound beam passing through a material with inhomogeneous index of refraction variations can be weakly lensed as it propagates through the material. This lensing effect changes depending on the imaging angle as the beam propagates through a different set of structures (and corresponding indices of refraction). Changes induced by these effects may be referred to as index of refraction variations.

Imaging Volume Geometry

Ultrasound imaging often involves contact with an imaging volume in order to form an ultrasound image. As a result, the surface geometry of an imaging volume may constrain the possible orientations of the ultrasound probe during image acquisition. In particular, the surface geometry may limit the number of angles which can be probed by manually rotating an ultrasound probe.

Figures 3A, 3B, 3C:
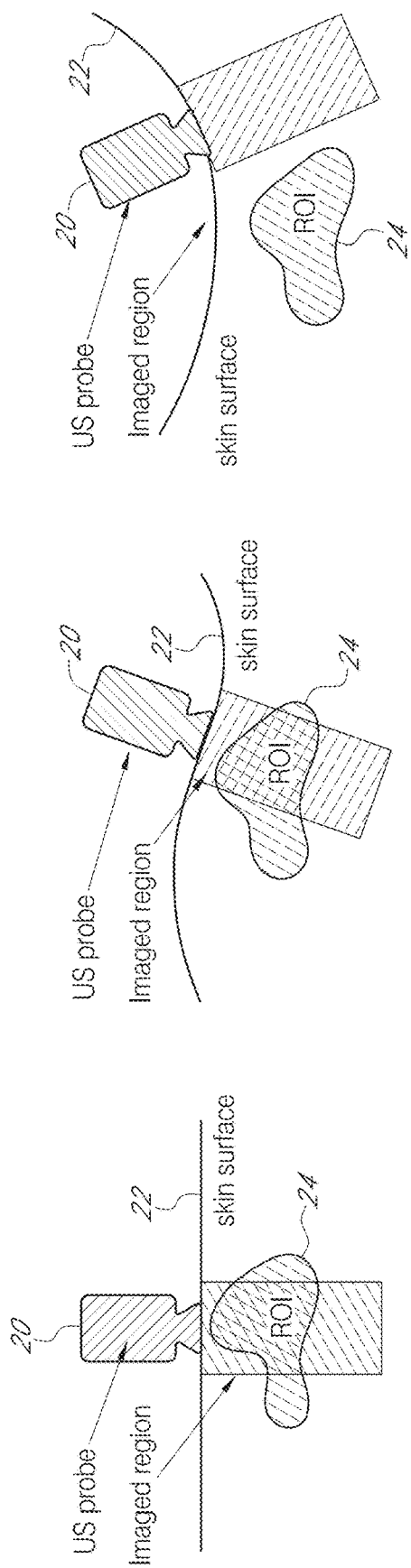
FIGS. 3A to 3C illustrate how the surface geometry of an imaging volume may affect the number and quality of images that can be captured at different angles.

FIGS. 3A to 3C illustrate how the surface geometry of an imaging volume may affect the number and quality of images that can be captured at different angles. In FIGS. 3A to 3C, an ultrasound probe 20 is imaging an ROI 24 under a surface 22 of an object being imaged. As shown in FIG. 3A, a given region-of-interest below a flat skin surface 22 may be imaged at a 0 degree without introducing large operator-induced distortions. FIG. 3B illustrates how the ROI 24 can be distorted by the ultrasound probe 20 at different angles. As shown in FIG. 3B, imaging that same ROI 24 from an angle may involve the operator pressing the ultrasound probe 20 into the skin in a manner that distorts the skin surface 22 and the underlying ROI 24. The distortion illustrated in FIG. 3B may be similar to the operator-induced variations discussed in connection with FIG. 2A. Even though tissue can be distorted to help aim the ultrasound probe 20 at the ROI 24, the amount of distortion to point at the ROI 24 may be impractical. As shown in FIG. 3C, some geometries may make it difficult or impossible to image an underlying ROI 24 from a variety of angles, particularly if the tissue is too rigid to be distorted.

Figure 4C:
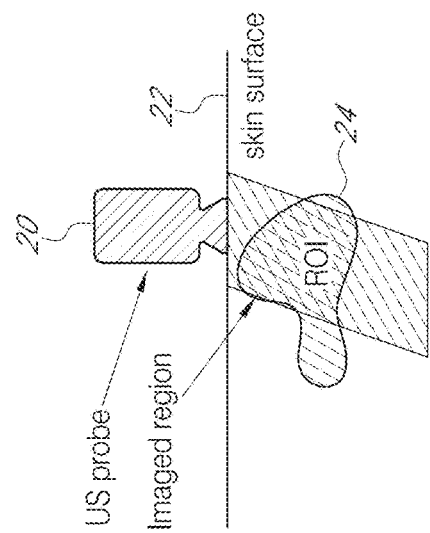
FIGS. 4A to 4C illustrate imaging an ROI from different angles using both manual rotation of a fixed probe and beam steering.
Figure 4B:
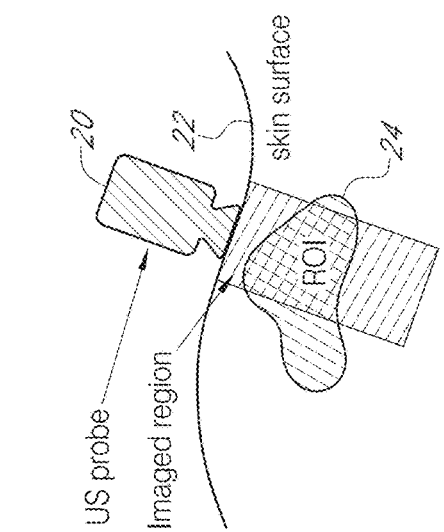
Figure 4A:
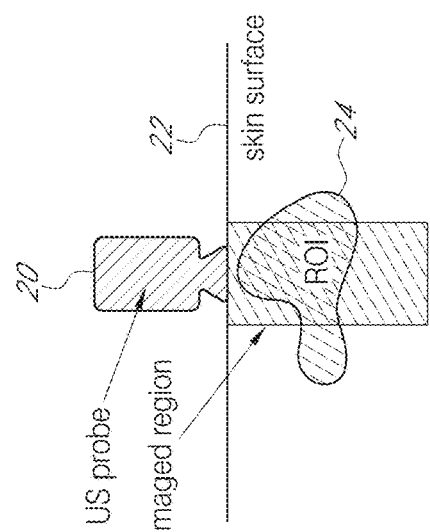

In at least some embodiments, imaging an ROI from different angles may be accomplished using manual rotation of an ultrasound probe, using beam steering, or using a combination of these and/or other techniques. FIGS. 4A to 4C illustrate imaging an ROI from different angles using both manual rotation of a fixed probe and beam steering. The beam steering method can allow the operator to follow the imaging volume surface horizontally. This can reduce distortion of the ROI.

As shown in FIG. 4A, an ROI 24 below a flat skin surface 22 may be imaged at a 0 degrees using an ultrasound probe 20. To image the same ROI 24 at a 20 degree angle, the ultrasound probe 20 may be manually rotated, distorting the skin and potentially distorting the ROI 24, for example, as shown in FIG. 4B. As shown in FIG. 4C, the same ROI 24 may be imaged at a 20 degree angle without distorting the skin or ROI 24 by using beam steering techniques. The ultrasound probe 20 can include a phased array to implement beam steering. A combination of beam steering and manual ultrasound probe rotations may be used.

In at least some embodiments, a system is provided that tracks an ROI (e.g., using software) and uses this tracking information to drive a ultrasound phased array to steer the ultrasound beam to image the ROI. Accordingly, the ultrasound probe can image an ROI from a number of angles without the operator physically rotating the ultrasound probe to these angles. As noted above, rotating the ultrasound probe may be difficult or impossible and/or induce undesirable distortions in an ultrasound image.

Ultrasound Imaging Systems

Ultrasound imaging systems with combined frequency and angle compounding and non-rigid image registration are disclosed. In some instances, ultrasound imaging systems can generate ultrasound images with reduced speckle in real time. Some other ultrasound imaging systems can perform post processing to generate ultrasound images with reduced speckle. Any suitable principles and advantages of the ultrasound imaging systems disclosed herein can be implemented together with each other. Any of the imaging processing operations described with reference to FIGS. 5A to 5D can be performed by one or more suitable computing devices.

Figure 5A:
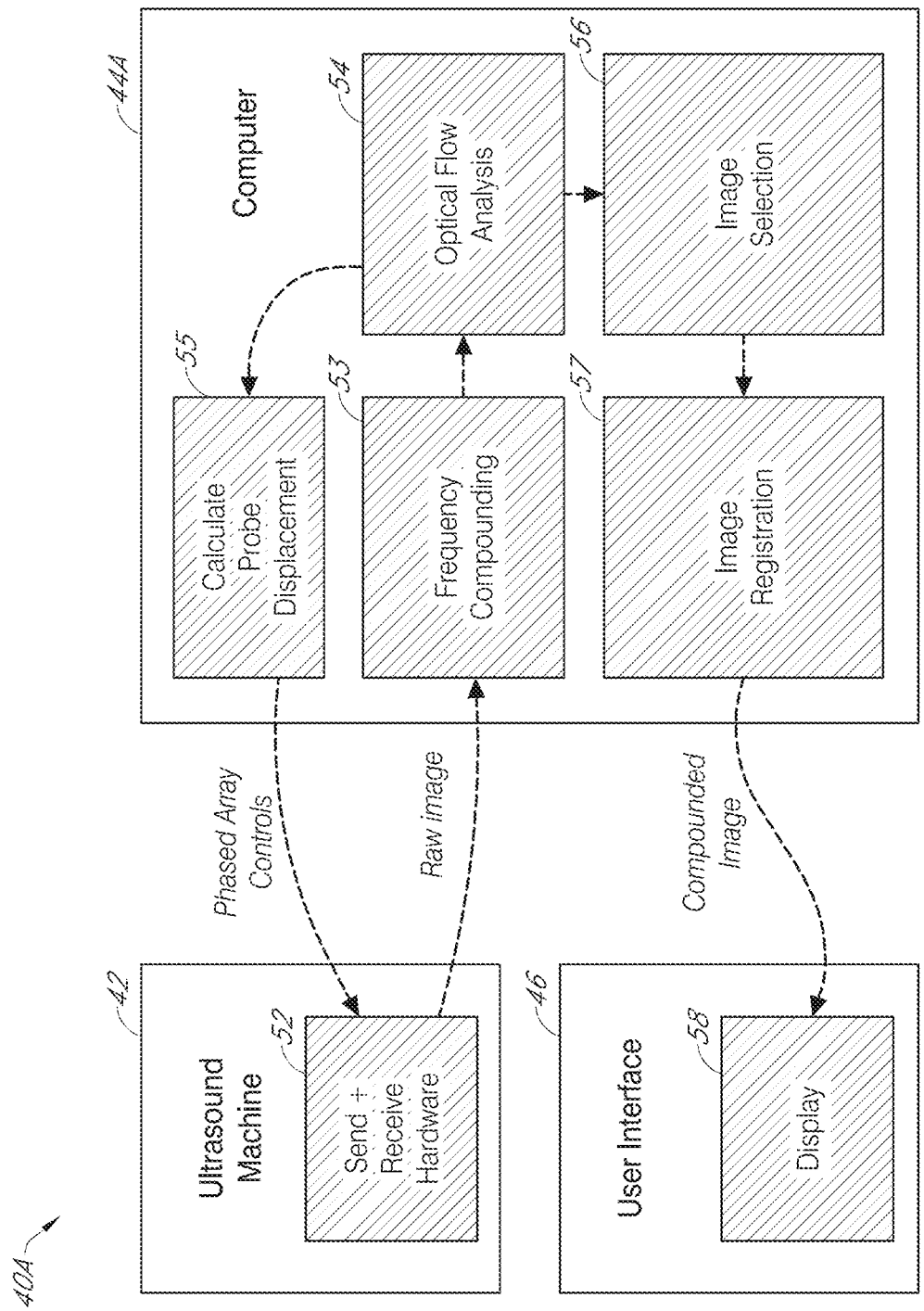
FIG. 5A illustrates an ultrasound imaging system according to an embodiment.

FIG. 5A is a schematic block diagram of an ultrasound imaging system 40A according to an embodiment. A framework for ultrasound imaging with reduced speckle with be described with reference to FIG. 5A. This framework uses image processing to track a ROI to control an ultrasound device and registers and compounds images for speckle reduction. The disclosed techniques can be broken down into a series of image processing and analysis operations that interface with ultrasound hardware to analyze and control the ultrasound imaging operations.

The illustrated ultrasound imaging system 40A includes an ultrasound probe 42, a computing device 44A, and a user interface 46. The ultrasound probe 42 can be any suitable ultrasound probe arranged to transmit an ultrasound beam to an object being imaged and receive echoes from the object being imaged. The ultrasound probe 42 can include a phased array. The phased array can steer an ultrasound beam. The ultrasound probe includes send and receive hardware 52. The send and receive hardware 52 can generate ultrasound beams, receive echoes, and generate raw ultrasound image data. The ultrasound probe 42 can include one or more sensors that provide position and/or movement information about the ultrasound probe 42. Examples of such sensors include inertial sensors, vertical sensors, and the like.

The computing device 44A can be implemented by one or more suitable computing devices arranged to process raw ultrasound image data and output compounded ultrasound image data. For example, the computing device 44A can include a laptop, a desktop computer, a smart phone, an image processing module, the like, or any suitable combination thereof. In certain embodiments, the computing device 44A can be implemented by two or more separate computing devices that are together arranged to implement the functionality described with reference to the computing device 44A. The computing device 44A can include one or more processors arranged to perform the image processing functionality described herein. Any portion or all of any of the image processing operations and/or algorithms disclosed herein can be performed in association with specific instructions stored on a non-transitory computer-readable storage medium executed by one or more processors. One or more physical devices can implement any of the computing devices disclosed herein, such as the computing device 44A.

As illustrated, the computing device 44A includes a frequency compounding block 53, an optical flow processing block 54, a probe displacement block 55, an image selection block 56, and an image registration block 57. The computing device 44A can include dedicated signal processing circuitry to perform any suitable functionality of one or more of the illustrated blocks. The computing device 44A can include instructions stored in memory that cause one or more processors to perform any suitable functionality of one or more of the illustrated blocks.

The user interface 46 can present an ultrasound image with reduced speckle. The user interface 46 can include a display 58.

The send and receive hardware 52 of the ultrasound probe 42 can transmit an ultrasound beam to an object being imaged, receive echoes of the transmitted ultrasound beam from the object being imaged, and generate raw image data from the echoes. The ultrasound beam can include ultrasound pulses. A stream of raw ultrasound image data may be sent from the ultrasound probe 42 to the computing device 44A. The stream can be continuous.

The frequency compounding block 53 can frequency compound the raw ultrasound image data to generate frequency compounded ultrasound image data. For example, using a set of digital filters, the frequency compounding block can normalize and compound ultrasound images across a number of frequency bands. Frequency compounding ultrasound images can reduce speckle.

The frequency compounded images are provided to an optical flow processing block 54. The optical flow analysis block 54 can track motion of the ultrasound probe 42 between successive frames. This information can be provided to the probe displacement block 55. The optical flow analysis block 54 can determine a spatial location of an ROI. The probe displacement block 55 can calculate the displacement of the ultrasound probe 42. The calculated probe displacement can include a change in position of the ultrasound probe 42 and/or a change of an angle at which the ultrasound probe 42 is imaging an ROI. The probe displacement block 55 can provide one or more control signals to the ultrasound probe 42. The one or more control signals can include phase array control signals that provide updated commands for a phased array of the ultrasound probe 42. This can direct the ultrasound probe 42 to steer an ultrasound beam to the ROI being imaged.

The probe motion estimation generated by the optical flow analysis block 54 can also be used to calculate an approximate angular displacement between frames by the image selection block 56. Alternatively, the image selection block 56 can determine an approximate angular displacement of the ultrasound probe 42 based on the frequency compounded ultrasound image data. Once the angular displacement passes a given threshold, an image can be captured and passed to the image registration block 57. The image registration block 57 can register images and perform angle compounding. The image registration block 57 can execute a non-rigid image registration algorithm to register the new image with one or more previously captured frames. The compounded image generated by the image registration block 57 can have low speckle. As discussed above, angle compounding together with frequency compounding can have a multiplicative effect in terms of reducing speckle in an ultrasound image.

The compounded image generated by the image registration block 57 can be stored in non-transitory computer storage and/or presented to a user. The compounded image can be provided to at the user interface 46. The user interface 46 can present the compounded image to the user, for example, via the display 58.

Figure 5B:
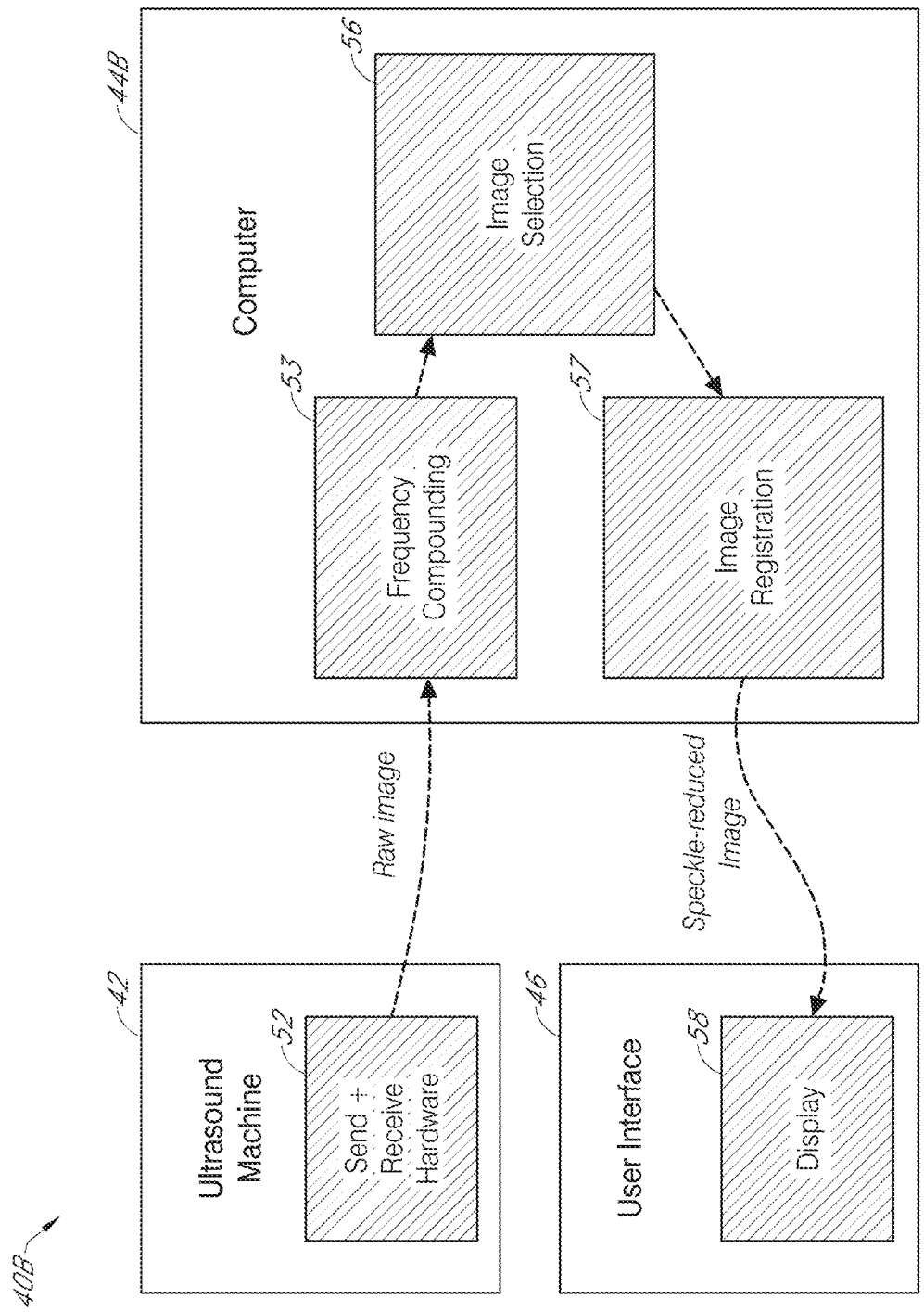
FIG. 5B illustrates an ultrasound imaging system according to another embodiment.

FIG. 5B is a schematic block diagram of an ultrasound imaging system 40B according to an embodiment. The ultrasound imaging system 40B includes a computing device 44B that is configured to execute different image processing than the computing device 44A of FIG. 5A. As illustrated, the computing device 44B includes a frequency compounding block 53, an image selection block 56, and an image registration block 57. The image selection block 56 in the computing device 44B can estimate approximate angular displacement of the ultrasound probe 42 based on the frequency compounded ultrasound image data from the frequency compounding block 53. The image selection block 56 can select ultrasound images to register and spatially compound based on the determined angular displacement. The image selection block 56 can perform a cross-correlation between ultrasound images. The cross-correlation can indicate whether and by how much ultrasound images can overlap with each other. The selected ultrasound images can be registered and spatially compounded by the image registration block 57. The computing device 44B can process raw ultrasound image data provided by the ultrasound probe 42 without directing the ultrasound probe 42. FIG. 5B illustrates that some ultrasound imaging systems can be implemented without a computing device providing information to the ultrasound probe 42 for beam steering and/or capturing images.

Figure 5C:
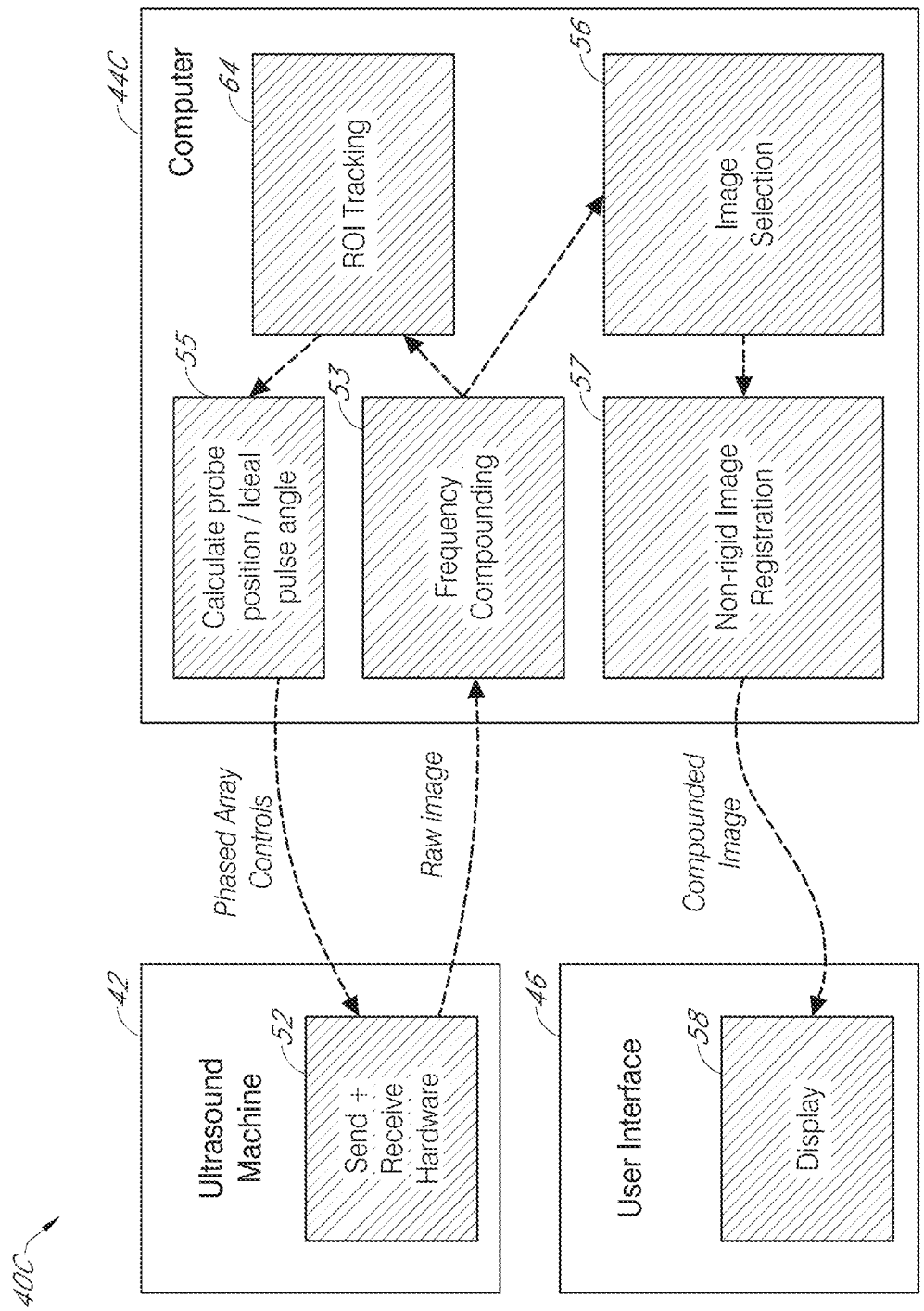
FIG. 5C illustrates an ultrasound imaging system according to another embodiment.

FIG. 5C is a schematic block diagram of an ultrasound imaging system 40C according to an embodiment. The ultrasound imaging system 40C includes a ROI tracking block 64. The ROI tracking block 64 can track motion of the ultrasound probe 42 between successive frames. The ROI tracking block 64 can use data from an inertial sensor of the ultrasound probe 42, a vertical sensor of the ultrasound probe 42, optical tracking, or any suitable data indicative of a displacement angle of the ultrasound probe 42. The optical tracking flow block 54 of FIG. 5A is one example of the ROI tracking block. FIG. 5C illustrates that the frequency compounded ultrasound frequency compounded ultrasound image data from the frequency compounding block 53 can be provided to both the ROI tracking block 64 and the image selection block 56. Alternatively or additionally, data generated by the ROI tracking block 64 can be provided to the image selection block 56.

Figure 5D:
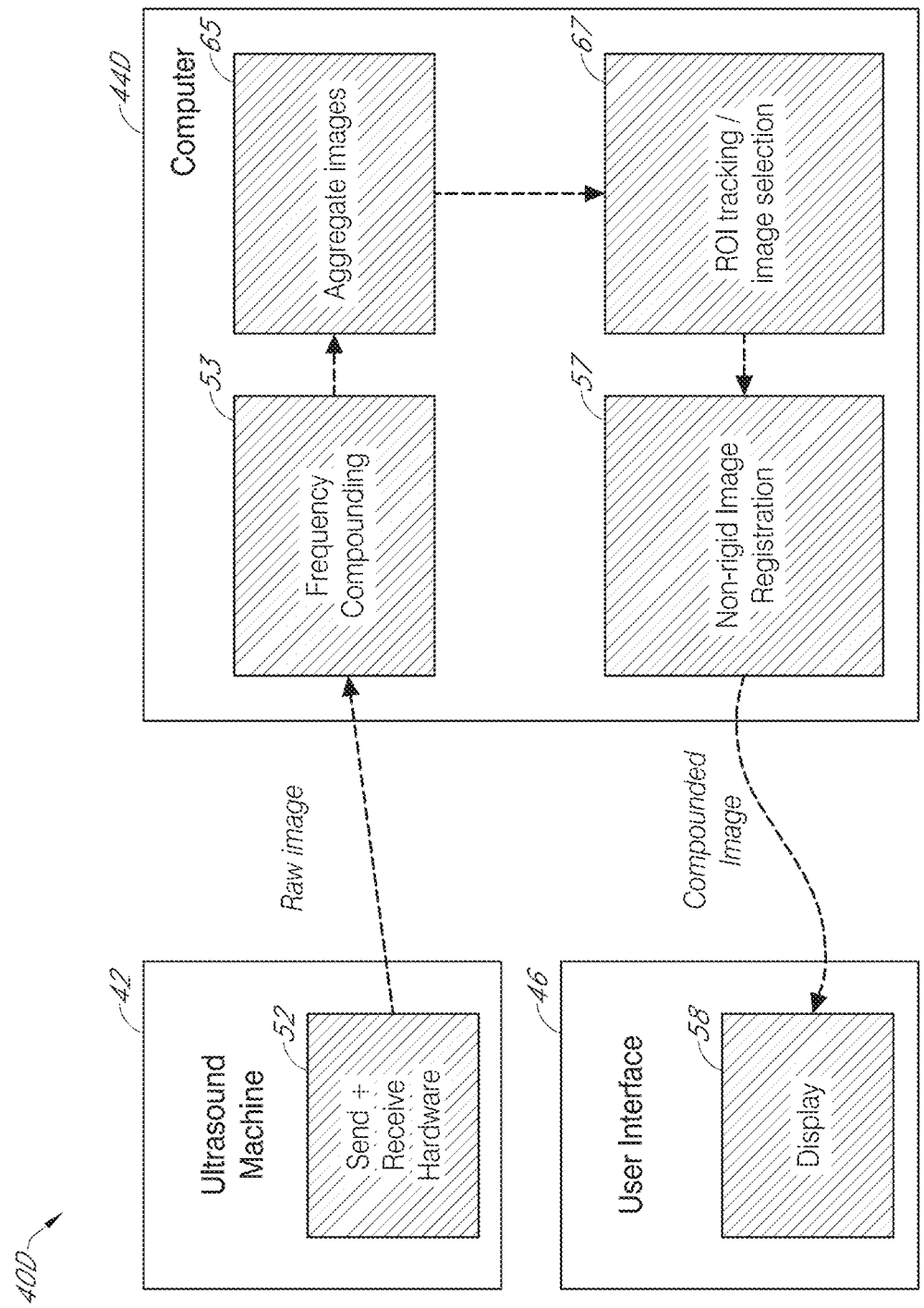
FIG. 5D illustrates an ultrasound imaging system according to another embodiment.

FIG. 5D is a schematic block diagram of an ultrasound imaging system 40D according to an embodiment. The ultrasound imaging system 40D can perform post processing to generate a compounded ultrasound image with reduced speckle. The ultrasound probe 42 can capture a sweep of ultrasound image data in a scan.

The computing device 44D of the ultrasound imaging system 40D includes a frequency compounding block 53, an image aggregation block 65, and ROI tracking and image selection block 67, and an image registration block 57. The ultrasound probe 42 can provide raw ultrasound image data to the frequency compounding block 53 for frequency compounding. Frequency compounded ultrasound image data from the frequency compounding block 53 can be provided to the image aggregation block 65. The image aggregation block 65 can aggregate a large number of images including images for areas outside of an ROI being imaged. The ROI tracking and image selection block 67 can reduce the large number of images from the image aggregation block 65. This can involve determining that images correspond to an ROI and correspond to angles that differ by a threshold amount. The ROI tracking and image selection block 67 can perform a cross-correlation between ultrasound images to determine that images correspond to an ROI. The cross-correlation can indicate whether and by how much ultrasound images can overlap with each other. With the ROI tracking and image selection block 67, a large data set can be reduced to a manageable amount of data for image registration and angular compounding. The image registration block 57 can perform non-rigid image registration and angular compounding.

Figure 5E:
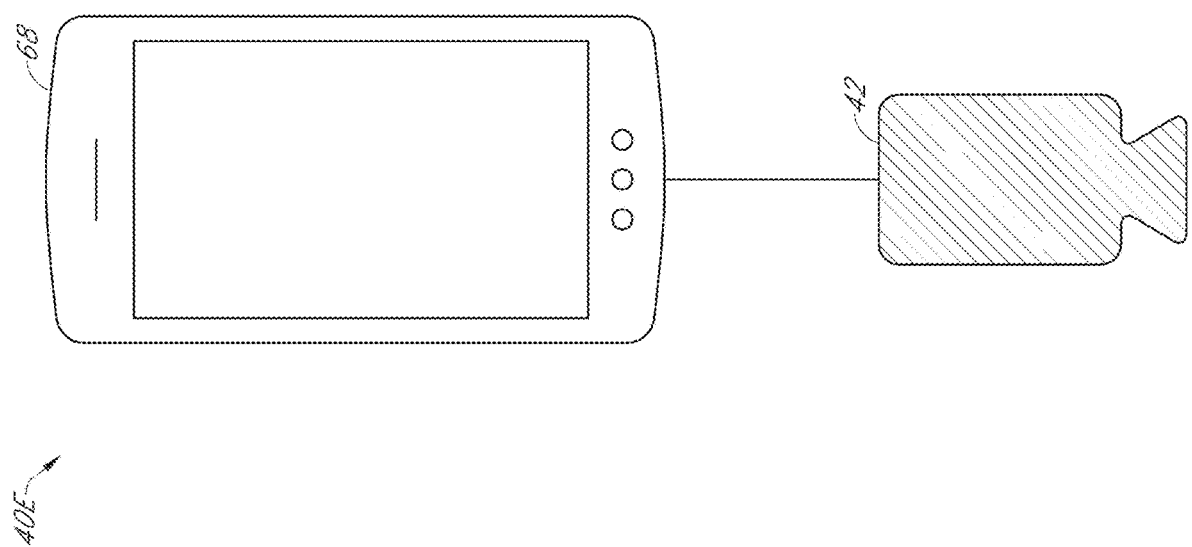
FIG. 5E illustrates an ultrasound imaging system according to another embodiment.

An ultrasound probe can be in communication with any suitable computing device that can execute image processing to perform frequency and angle compounding. FIG. 5E illustrates an ultrasound imaging system 40E that includes an ultrasound probe 42 in communication with a mobile phone 68. The ultrasound probe 42 can provide raw ultrasound image data to the mobile phone 68. The mobile phone 68 can perform some or all of the image processing described herein. In some instances, the mobile phone 68 can wirelessly communicate data to one or more other computing devices to perform some or all of the image processing disclosed herein. Alternatively or additionally, the mobile phone 68 can communicate data to one or more other computing devices via a wired connection to perform some or all of the image processing disclosed herein. The mobile phone 68 can be connected to the ultrasound probe 42 via a wired connection as illustrated and/or via a wireless connection.

Frequency Compensation

Ultrasound transducers typically have limited frequency response. Even broadband transducers have Q-factors of $Q \equiv f/\Delta f < 1.5$ (e.g., Q-factors of less than about 1.5). We can compensate for the finite Q of the transducer by digitally generating a relatively short radio frequency (RF) pulse with a frequency spectrum with enhanced amplitudes in the portions of the spectrum where the frequency response is declining. The desired radio frequency pulse with a flat-topped frequency spectrum can be created by converting the digital waveform to an analog radio frequency pulse with a digital-to-analog converter. Compensation of any non-linear frequency response of the transducer may also be fine-tuned by altering the digital signal. For example, a compensation function can be calculated by inverting an impulse response of the transducer (e.g., Green's function). Gaussian smoothing can be applied to the inverse of the impulse response of the transducer. The frequency compensation can shape a pulse transmitted by an ultrasound probe. The send and receive hardware 52 of the ultrasound probe 42 in any of FIGS. 5A to 5D can generate the radio frequency pulse.

Different frequency images are created by Fourier transforming the full time record of the flat-topped broadband ultrasound echo signal into frequency space. The Fourier transformed signal can be divided into a set of narrower-band digitally filtered signals centered at different frequencies. The filtering can be performed with digital Gaussian filters. Each filtered spectrum can be Fourier transformed back into the time domain to create images centered at different frequencies. Accordingly, a single ultrasound pulse can be used to create a set of separate images centered at different frequencies. The separate images are compounded to form the reduced-speckle image. Any of these operations can be performed by the frequency compounding block 53 of any of the compounding devices 44A to 44D of FIGS. 5A to 5D, respectively. A frequency compounding block can perform any suitable operations to create ultrasound images at different frequencies and then perform frequency compounding on such ultrasound images.

Frequency Compounding

Fast Fourier transform operations can be performed to enable real time frequency compounding. In at least some embodiments, fast Fourier transform (FFT) operations may be performed in real time on a dedicated chip. In various other embodiments, fast Fourier transform operations may be performing using one or more application-specific integrated circuits (ASICs), one or more microprocessors, one or more programmable integrated circuits such as field-programmable gate arrays (FPGAs), or other hardware. The frequency space images can be discretized as discussed herein (e.g., as discussed in connection with compensating for the finite Q of ultrasound transducers using a short radio frequency pulse with a frequency spectrum with enhanced amplitudes in the portions of the spectrum where the frequency response is declining). An inverse Fourier transform can be applied using the same fast Fourier transform hardware and the real space images can be compounded. The frequency compounding block 53 of any of the compounding devices 44A to 44D of FIGS. 5A to 5D, respectively, can perform frequency compounding.

Beam Steering

The ultrasound imaging system 40A of FIG. 5A and the ultrasound imaging system 40C of FIG. 5C include ROI tracking and beam steering. By combining ROI tracking with beam steering technology, we can facilitate angular compounding in situations where it is undesirable and/or impossible to move the ultrasound probe 42 through a suitable number of imaging angles. FIG. 4C illustrates the use of beam steering to capture multiple angles of an ROI 24 while reducing and/or minimizing operator-induced distortion.

Capturing an image using manual rotation (e.g., as shown in FIG. 4B) may be more difficult and can result in a less accurate image than when using a beam steering mechanism. Manual rotation may significantly distort the tissue, resulting in less consistent images across angles. Further, manual rotation may be difficult or impossible for more extreme angles and/or when imaging stiff tissues. As shown in FIG. 4C, beam steering can allow the operator to image a defined ROI 24 by changing the direction of the ultrasound beam to compensate for horizontal motion of the ultrasound probe 20 along the tissue surface 22. In certain embodiments, beam steering may be automatic in that an ultrasound imaging system (e.g., the ultrasound imaging systems 40A and 40C) automatically tracks a defined ROI by automatically adjusting the beam steering to compensate for motion of the ultrasound probe. In some other embodiments, beam steering may be a manual process in which an operator provides input to steer a beam.

ROI Tracking

In a framework for ultrasound imaging with reduced speckle disclosed herein, a set of ultrasound images that include an ROI or a portion of an ROI can be parsed. Then the spatial location of the ROI can be determined. The optical tracking flow block 54 of FIG. 5A and the ROI tracking block 64 of FIG. 5C are examples of ROI tracking blocks that can perform ROI tracking. The ROI location can be used to cull a large set of data, for example, in post processing embodiments such as the ultrasound imaging system 40D of FIG. 5D.

Any suitable ROI tracking algorithm can be implemented. For example, classical and machine learning based approaches can be implemented. Example ROI tracking algorithms include without limitation Boosting, kernelized correlation filter (KCF) tracker, multiple instance leaning (MIL), Generic Object Tracking Using Regression Networks (GOTURN), and fast optical flow analysis. For example, a KCF tracker algorithm can be used to track an ROI over a number of frames. The ROI tracking data is analyzed to determine an angle for the phase array probe to increase and/or maximize overlap with the ROI. This can be the angle from the center of the top of the image (where the probe head would be located physically) to the center of the ROI.

An example of ROI tracking is a fast optical flow analysis. The fast optical flow analysis of a continuous stream of ultrasound images captured by the ultrasound device enables both the ROI tracking and beam steering and image selection routines.

An ROI tracking algorithm, which can be executed by one or more computing devices programmed with specific instructions, can be applied to the stream of incoming ultrasound images. The ROI tracking algorithm can compute the relative displacement of one image from the previous. This can be used to track a ROI for beam steering and provide information about the relative displacement and rotation of a given image for image compounding and registration. In at least some embodiments, images can be significantly down sampled (e.g., by a factor of five times, ten times, or more than ten times) prior to computing the relative displacement of one image from another. Such down sampling may reduce the computations of the ROI tracking algorithm, facilitating real time computation speeds. Moreover, the ROI tracking w algorithm may still be able to determine the translations and rotations of the ROI between two images with sufficient accuracy when analyzing down sampled images. In at least some embodiments, the amount of down sampling utilized may be a tradeoff between computational speed (which may depend on available computational resources) and accuracy in approximating the relative displacement of one image to another image.

The ROI tracked by the ROI tracking (e.g., optical flow analysis) can be used to direct a beam steering routine. The beam location may be updated at each image step to compensate for the motion of the ultrasound probe relative to the ROI.

Image Selection

An algorithm, which can be executed by one or more computing devices, can select images for compounding from the stream of ultrasound images which match a pre-defined criteria. An example of a predefined criterion is a threshold for angular displacement from one or more previous ultrasound images being met. Attempting to register all images may be too computationally expensive and/or may preclude real-time performance, in at least some embodiments. In some other embodiments, computational resources may permit registering of all images while maintaining real-time performance. An image selection block (e.g., the image selection block 56 and/or 67 discussed above) allows the ultrasound imaging system to select images to improve and/or maximize speckle reduction, without overloading available computational resources.

Not all images captured need to be compounded in certain applications. To balance speckle reduction in the ultimate image with computational load (which may be helpful in providing real time performance), an algorithm to filter incoming images and select the images that will increase and/or maximize speckle reduction across a ROI is provided. At the same time, the algorithm can reject images that have lower and/or minimal value to speckle reduction. Because speckle is typically correlated with the angle of the incident beam, it may be beneficial to select a set of images where each is separated from the others by at least a predefined rotation. We can keep track of the angle of images that have been captured and select only images from the image stream whose angles of incidence on the ROI are above or below a given threshold.

If the ROI is larger than the ultrasound probe field of view than multiple images at each angle can be captured and stitched together to cover the ROI. This can be accomplished by segmenting the ROI and keeping individual records of angles captured for each segment.

A user interface, such as an output monitor and/or the user interface 46 of FIGS. 5A to 5D, can prompt the user to move the ultrasound probe to a given position if more images are needed from a particular direction. In at least some embodiments, the system may include a component that identifies from which angles images have already been captured and/or from which angles images are needed. The system may also display or otherwise present such information to a user, such that the user can easily determine which angles they should capture additional images from to further reduce speckle in an efficient manner.

Non-Rigid Image Registration

Automatic registration can be implemented with a suitable number of degrees of freedom to compensate for non-rigid distortions of the object; such as the operator-induced variations, the patient-induced variations, and the index of refraction variations discussed in connection with FIGS. 2A to 2C.

An image registration framework to align an arbitrary number of ultrasound images is provided herein. An example implementation of this framework includes an iterative registration algorithm. Such an algorithm is not the only way to register ultrasound images, and the disclosed technology applies to any suitable algorithm implemented in a suitable speckle reduction framework, such as in any of the ultrasound imaging systems of FIGS. 5A to 5D. The image registration block 57 can execute any suitable image registration algorithm for registering ultrasound images.

With reference to FIGS. 6A to 6C, an example of non-rigid image registration will be described. FIG. 6A illustrates a first image 70A. FIG. 6B illustrates a second image 70B. The first image 70A and the second image 70B can correspond to the same ROI. The second image 70B can be elastically distorted relative to the first image 70A. The non-rigid image registration can involves applying a transformation to elastically distort the second image 70B to map to the first image 70A. Non-rigid image registration of the second image 70B to the first image 70A can generate a registered image 70C that is shown in FIG. 6C. The non-rigid image registration can be implemented with any suitable principles and advantages of non-rigid image registration disclosed herein.

More information including math related to images and image registration will now be provided. An image $I(x_i, y_i)$ can be defined as a discretely sampled function on a coordinate space $R^2 = \{x_i, y_i\} \rightarrow R^n$, where the set $\{x_i, y_i\}$ are the coordinates of an array of pixels representing the image, and $R^n$ are the n "color" values for each pixel $x_j, y_j$. In the case of ultrasound imaging, the image is monochromatic and n=1. Two different images then represent two maps on two different coordinate spaces. An image transform that allows the registration of two images can be defined as the coordinate transformation $T(x, y): R^2 \rightarrow R^2$. In the case of a rigid translation, $T(x, y): (x, y) \rightarrow (x+\delta x, y+\delta y)$. The transform T is used to synthesize a new image $I'((x_i, y_i) = I(T(x_i, y_i)) = I(x'_i, y'_i)$. For the rigid translation given above, $I' = I(x+\delta x, y+\delta y)$.

A goal of an image registration algorithm is to find a transformation T that maps points in the coordinate space from one image onto the coordinate space of another image. For example, in the case of Cartesian registration a transformation T can be thought of as a three dimensional vector corresponding to changes in rotation, vertical displacement, horizontal displacement. One of the images is selected to be a "stationary" image S defined in its coordinate system. The other image is designated as M, the "moving" image. The transformation T shifts the coordinates of S, $(x_i, y_i)$ to the coordinates of M, $(x'_i, y'_i)$. If there is a perfect correlation and registration between the two images, $S(x, y) = M(T(x, y))$. Accordingly, under a perfect registration, the moving and transformed reference images are identical. For convenience, we define $M' \equiv M(T(x, y))$.

Figure 7A:
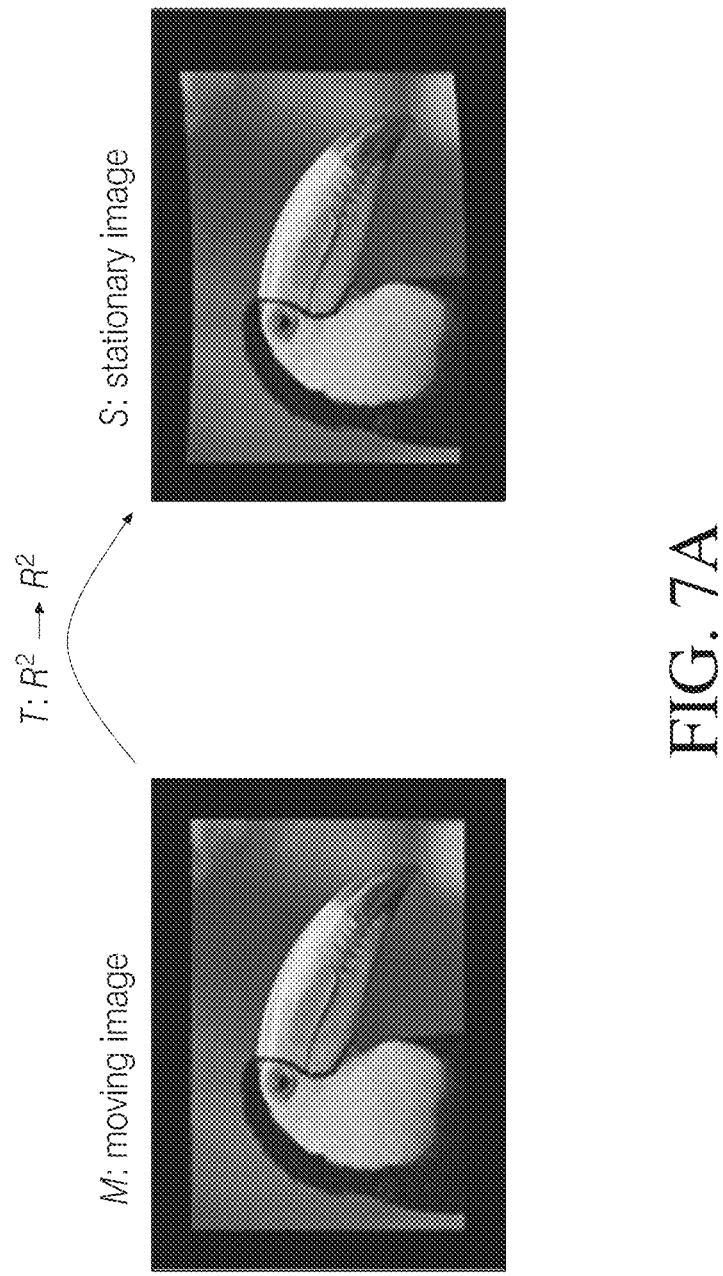
FIG. 7A illustrates a moving image to be transformed to a stationary image for non-rigid image registration.

The non-rigid image registration problem is illustrated in FIG. 7A. In FIG. 7A, images of a toucan bird are shown. A moving image M is transformed to a stationary image S in non-rigid image registration. While the present disclosure relates to ultrasound images with monochrome images, colors in the examples are kept and it is assumed that the corresponding grayscale values are used for image matching. Note that margins with zero-pixel values have been appended to the images M and S to allow for distortions that are outside the original image boundaries. The transform T in this example is parameterized by a set of displacement vectors $\{a_i\}$ which map each image pixel $p' = (x, y)$ in the translated image M' to a corresponding point in the moving image M. In other words, the vectors $\{a_i\}$ represent a discretized transformation T that constructs an image by sampling the moving image M such that the intensity value at p' in the transformed image M' is given by the value at p in the moving image M with $p = p' + a_i$.

Figure 7B:
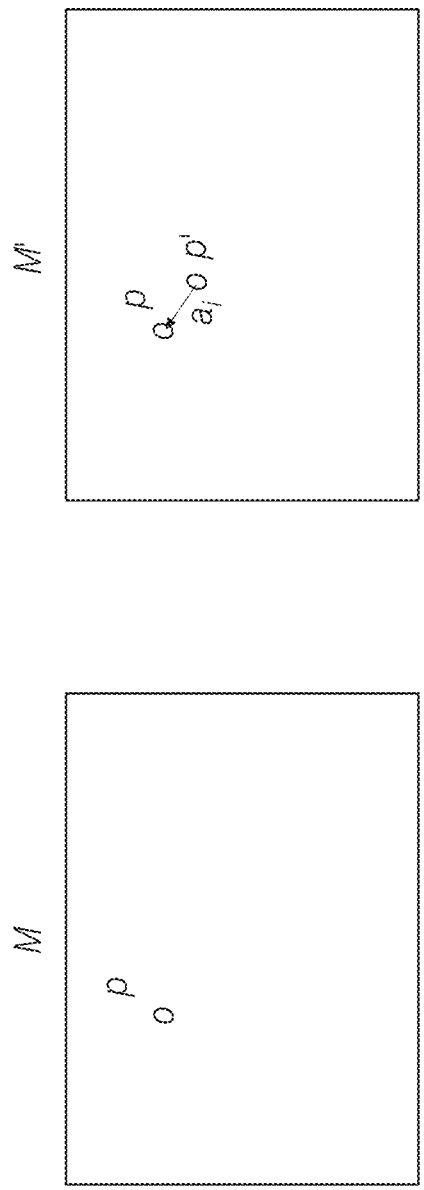
FIG. 7B illustrates a displacement vector for mapping a pixel in non-rigid image registration.
Figure 7C:
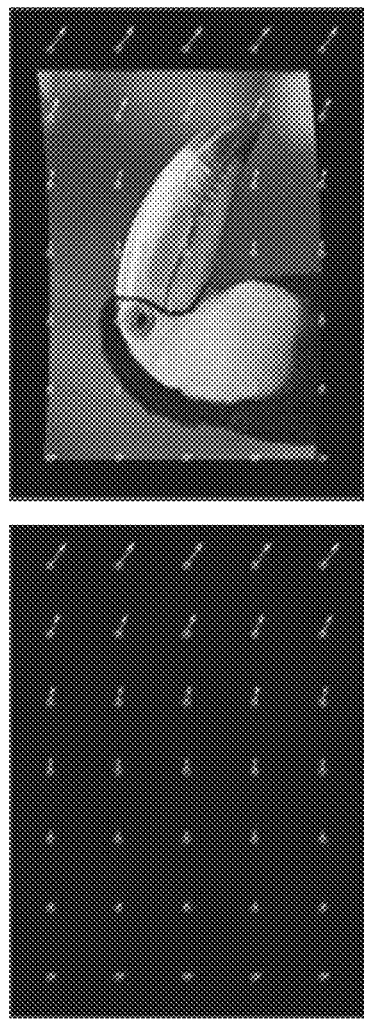
FIG. 7C illustrates a registered image and displacement vectors.

FIG. 7B illustrates a displacement vector $a_i$ that starts from p' in the translated image M'. The image value at p' is given by the image value at p in the moving image M. FIG. 7C shows the spatial distribution of a subset of the displacement vectors $\{a_i\}$ and the deformed image M'. The new moving image shown on the right side of FIG. 7C is obtained using the displacement vectors $\{a_i\}$ shown on the left side of FIG. 7C.

A non-rigid registration is a registration method which allows for local changes in geometry. This is useful when a good correspondence between images cannot be achieved using rigid manipulations. FIGS. 6A to 6C illustrate a situation in which non-rigid motion may be desired to achieve good registration, as well as with the images of FIG. 7A.

We consider iterative gradient-based methods for computing optimal registration parameters $\{a\}$. In contrast, direct registration techniques estimate registration parameters from images without an optimization framework. For example, some neural network or blockmatching based techniques estimate parameters with a single computational step. The iterative gradient-based methods for computing optimal registration parameters $\{a\}$ are capable of optimizing $\{a\}$ (or at least finding parameters $\{a\}$ that are sufficiently optimized) with regard to a metric which characterizes the goodness of the transformation, or equivalently, the correspondence of the transformed and reference coordinates. There are broadly two categories of metrics including feature-based and pixel-based metrics. Feature-based metrics measure the correspondence of a discrete number of salient points between different images. Pixel-based metrics consider the global image registration problem on a per-pixel basis, typically by comparing intensity or other proxy for information content.

We can re-frame the registration problem in the language of a generic optimization problem on an energy function $E(\{a\})=M(I_r, I_m \cdot T_{\{a\}})+R(T_{\{a\}})$.

The first term on the right hand side (M) is a registration metric, which measures the "goodness" or quality of registration, while the second term (R) is a regularization which penalizes unrealistic mappings.

Different iterative registration algorithms were investigated to correct for non-rigid distortions in ultrasound images. Such algorithms included (1) a "demons" algorithm implemented in the "imregdemons" function in MATLAB and (2) a gradient descent algorithm using the ADAM optimizer and implemented in Python. Table 1 below outlines these example algorithms. These algorithms show encouraging results.

TABLE 1

Outlines of example non-rigid image matching algorithms

| Demons algorithm | Gradient descent algorithm |
| --- | --- |
| The displacement vectors are initialized to be $a_i = \vec{0}$ for each pixel in M'. Vs is calculated with respect to the displacement vector $a_i$ | A group of 10 by 10 grid points $b_j$ are selected to parametrize and assigned with displacement vectors $b_j$. |
| Compute updated $a_i$'s by computing $da_i$ using optical flow (Eq. S1). Smooth $a_i$'s with a Gaussian spatial filter. Obtain M' using updated $a_i$ | Calculate the gradient of the loss function with respect to $b_j$, and compute the update vector $db_j$. Interpolate $b_j$ to obtain the displacement vectors $a_i$. Obtain M' using updated $a_i$ |

An example of the gradient descent algorithm will be described in more detail. In an example implementation, the image distortion may be parameterized by a grid of b-spline nodes. This parameterization as splines can be quickly computed using a graphics accelerator chip. This parameterization may be referred to as image warp parameterization.

The quality of registration may be measured as an L2 Mean Squared Error loss. This is fast to compute and conducive to gradient descent optimization.

Warp parameters can be constrained by a loss on the local deformation. This may be referred to as warp regularization. Consider a 1-dimensional (1D) implementation considering nearest neighbors where $k_i$ are the warp nodes:

$$L_R = \sum_{(images)} \sum_i (k_i - 1/2 * k_{i-1} - 1/2 * k_{i+1})^2 \quad (2)$$

This loss can be easily extended to 2-dimensions (2D). It can also be extended to account for longer range 'interactions' by adding additional terms to the inner sum and normalizing their coefficients to sum to −1.

A 2D regularization with arbitrary range interactions can be implemented as the square of a convolution across the grid of spline knots which parameterize the warping parameters. A modified 2D Hamming window can be used as the kernel where the central value is −1 and the other values in the kernel are normalized such that the sum of all the elements in the matrix is 0.

The regularization constraint may be relaxed towards the end of the registration sequence, as the warp parameters may be close to global minima and therefore relatively stable. This allows the algorithm to find the finest scale registration errors.

The example gradient descent implementation may use a multi resolution strategy. Initially, images can be down sampled and registered at a coarse level before moving up to a finer grain image. After each registration step, a metric can be used to determine if the algorithm has converged at a given coarseness level. This metric tracks the mean gradient size as a proxy for the level of convergence. When either the mean gradient or its first derivative fall below given thresholds, we may assume the algorithm has converged at a given resolution and proceed to a higher resolution.

The spline node grid may also be down sampled at each resolution level by the same factor as the images. This may reduce the complexity of the problem at higher levels and reduce the chances of over-fitting.

The Adam optimizer (e.g., the Adam optimization algorithm for machine learning) may be used to optimize registration parameters.

Our implementation can use Tensorflow for automatic parameter optimization and hardware acceleration.

Phase Front Modulation

In addition to frequency and angle, a speckle pattern may be varied (and hence reduced through compounding) by modulating the phase front within the imaging voxel. Phase front modulation changes the relative phases of the scattered light from the scatterers within the voxel and hence changes the speckle pattern. Averaging over these speckle patterns results in a reduction in speckle. Due to the possibility to detect both phase and amplitude in ultrasound, the phase front modulation may be achieved without the use of a phase mask (e.g., a phase filter on the receiving end). A method of phase front modulation by digital processing of the received signals is provided herein.

Before describing the details of phase front modulation, a brief discussion of the ultrasound B-mode imaging process with dynamic receive focusing is provided.

Figure 8:
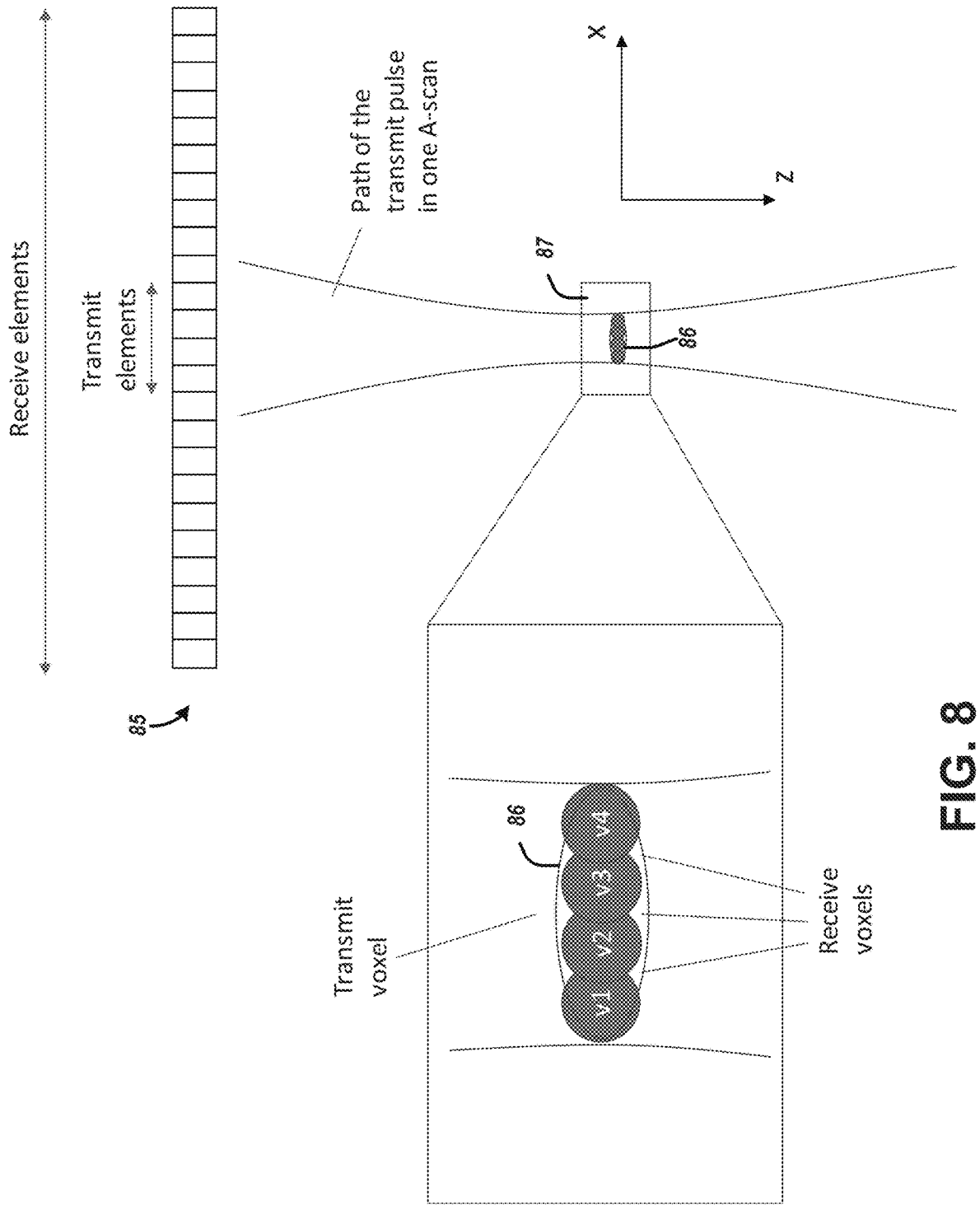
FIG. 8 illustrates an example an A-scan imaging tissue using transducer elements.

FIG. 8 illustrates an example an A-scan imaging tissue using transducer elements. FIG. 8 illustrates transducer elements 85 of an ultrasound transducer imaging an ROI 86 of tissue 87. The ROI 86 includes a transmit voxel and receive voxels $v_1$, $v_2$, $v_3$, and $v_4$. FIG. 8 includes a zoomed in view of the ROI 86. The transducer elements 85 can form a phased array. In an A-scan, a single ultrasound pulse can be transmitted with a subset of the transducer elements 85. A larger set of the transducer elements 85 can be used for receiving. This can result in receive voxels $v_1$, $v_2$, $v_3$, and $v_4$ having a higher lateral resolution than the transmit voxel.

In forming a B-mode image, a series of line scans (A-scans) can be performed. In each A-scan, an ultrasound pulse is transmitted. At each location along the path of the pulse, the axial and lateral resolutions can define a transmission voxel. The axial resolution is given by the time duration of the sound pulse $\Delta z = \Delta t/c$, where c is the speed of sound, and the lateral resolution is determined by the transmit numerical aperture $\Delta x = \lambda/(2NA_t)$. To obtain an extended depth of focus in the transmission, a relatively small subset of the transducer array elements 85 can be used such that $NA_t$ is typically smaller than 0.2. When detecting the echo from a certain depth z along the transmission path, a larger subset or all of the transducer array elements 85 can be used, which gives a receive numerical aperture $NA_r$ larger than $NA_t$ and results in a tighter focus. The different path lengths from the receive voxel to the individual transducer elements, or channels, are compensated by applying a time delay to each channel. In basic ultrasound imaging, there can be a single receive voxel for each transmit voxel.

To perform phase front modulation, we can place more than one receive voxels within the transmit voxel through receive focusing. The optimal number of receive voxels depends on the ratio $NA_r/NA_t$ and is typically in the range of $NA_t/NA_r$ and $2NA_t/NA_r$. In an example embodiment corresponding to FIG. 9, we consider 4 receive voxels $v_1$, $v_2$, $v_3$, and $v_4$ within a transmit voxel. The receive voxels $v_1$, $v_2$, $v_3$, and $v_4$ move with the transmit voxel as the pulse propagates into the medium. For each A-scan, there are then four signal streams $A_1(t)$, $A_2(t)$, $A_3(t)$, and $A_4(t)$ digitized corresponding to the four receive voxels at each time delay. Additional phase delays $\phi_1$, $\phi_2$, $\phi_3$, and $\phi_4$ are applied to each of these signals, which encode a wavefront modulation. Here we consider the simplest case of binary phase delays of either 0 or $\pi$, even though more values between 0 and $2\pi$ may be used. To avoid an overall phase ambiguity, we set $\phi_1=0$. Hence there are a total of $2^3=8$ different phase fronts in this case.

Figure 9:
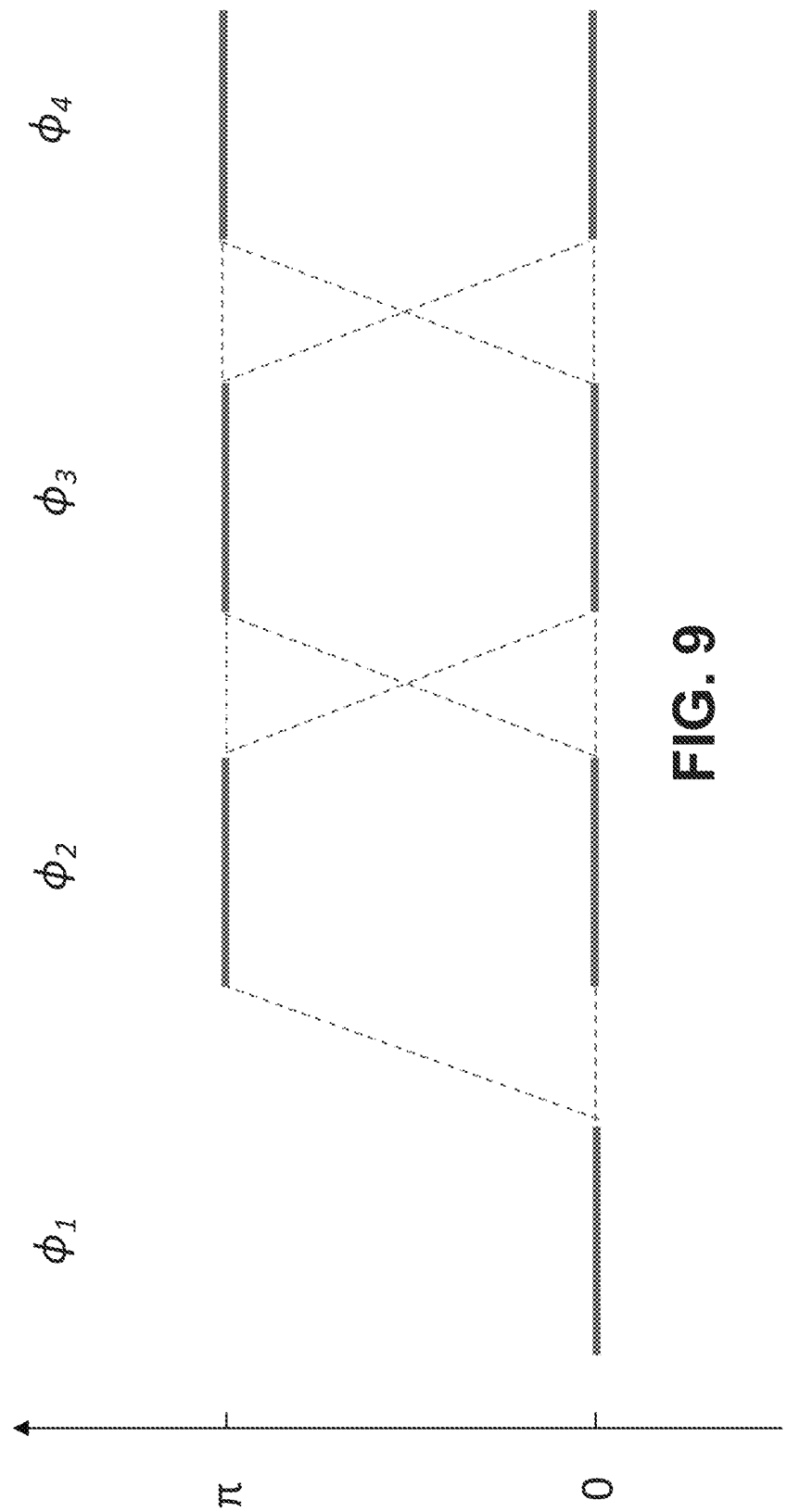
FIG. 9 illustrates phase delays that can be applied to receive signals corresponding to receive voxels.

FIG. 9 illustrates phase delays $\phi_1$, $\phi_2$, $\phi_3$, and $\phi_4$ that can be applied to receive signals A1, A2, A3, A4, corresponding to receive voxels v1, v2, v3, and v4, respectively. Since the overall phase does not affect the amplitude of the coherent sum of the signals from the receive voxels, we can set $\phi_1=0$. The dashed lines in FIG. 9 connect the phases of the voxels, indicating different ways to modulate the phase front.

Figure 10:
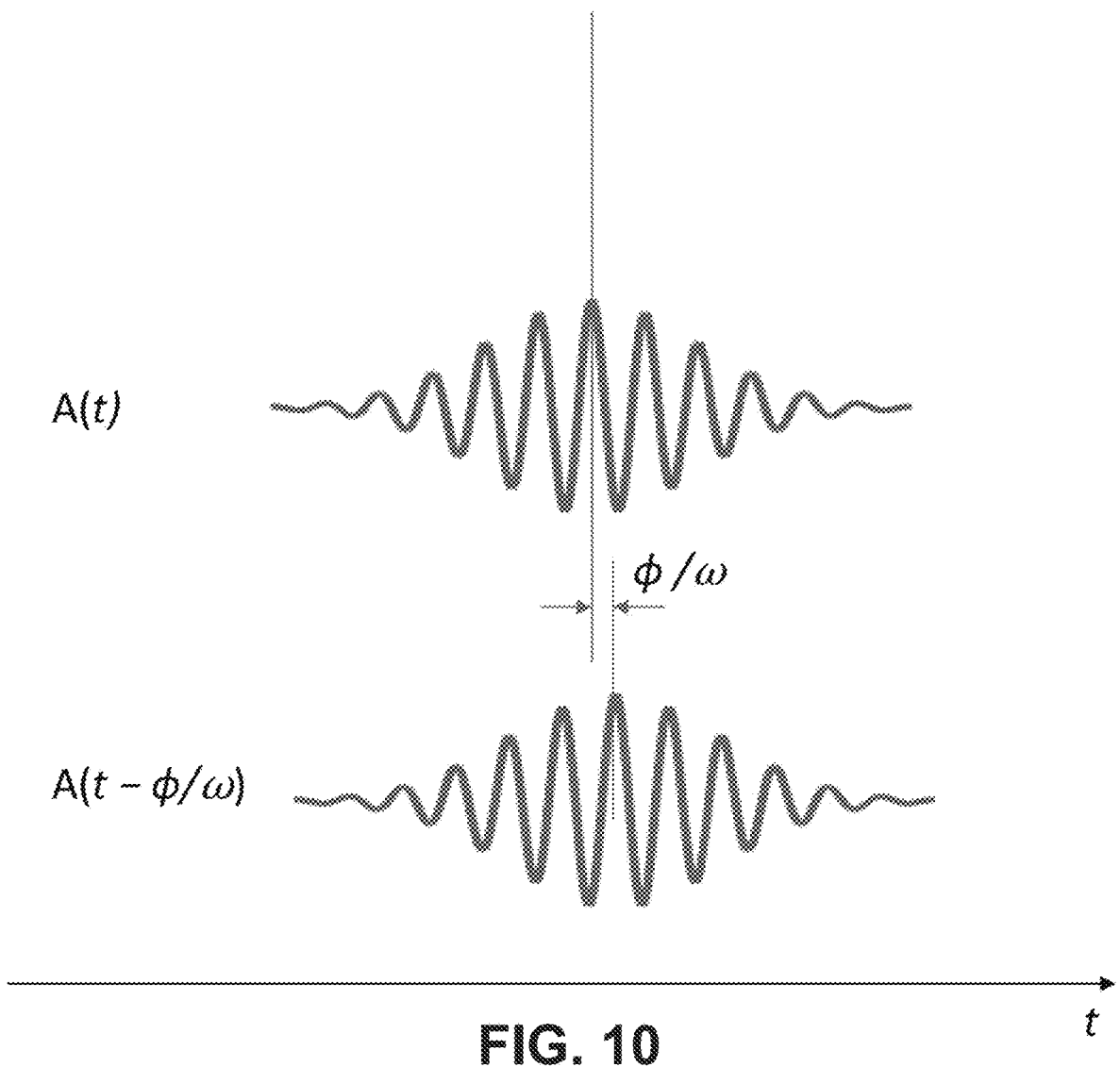
FIG. 10 illustrates applying a phase shift to a detected signal of a receive voxel.

The phase modulations can be achieved by applying a time delay to the signal streams. FIG. 10 illustrates applying a phase shift $\phi$ to a detected signal A of a receive voxel. A phase modulation $\phi$ corresponds to a time delay t of: $t=\phi/\omega$, in which $\omega$ is the center angular frequency of the sound pulse, Phase shifts can be similarly applied for the other receive voxels. The 8 different phase fronts produces 8 signal streams in receive, which can then be averaged after envelope detection. The speckle reduction is expected to be approximately $\sqrt{NA_t/NA_r}$.

EXPERIMENTAL RESULTS

We find that an algorithm according to an embodiment can align a pair of images with reasonable accuracy in about 3 seconds running on a single central processing unit (CPU) with one Nvidia k20 graphics processing unit (GPU). We believe with optimization of the algorithm we can align a set of images in less than a second.

Figure 11A:
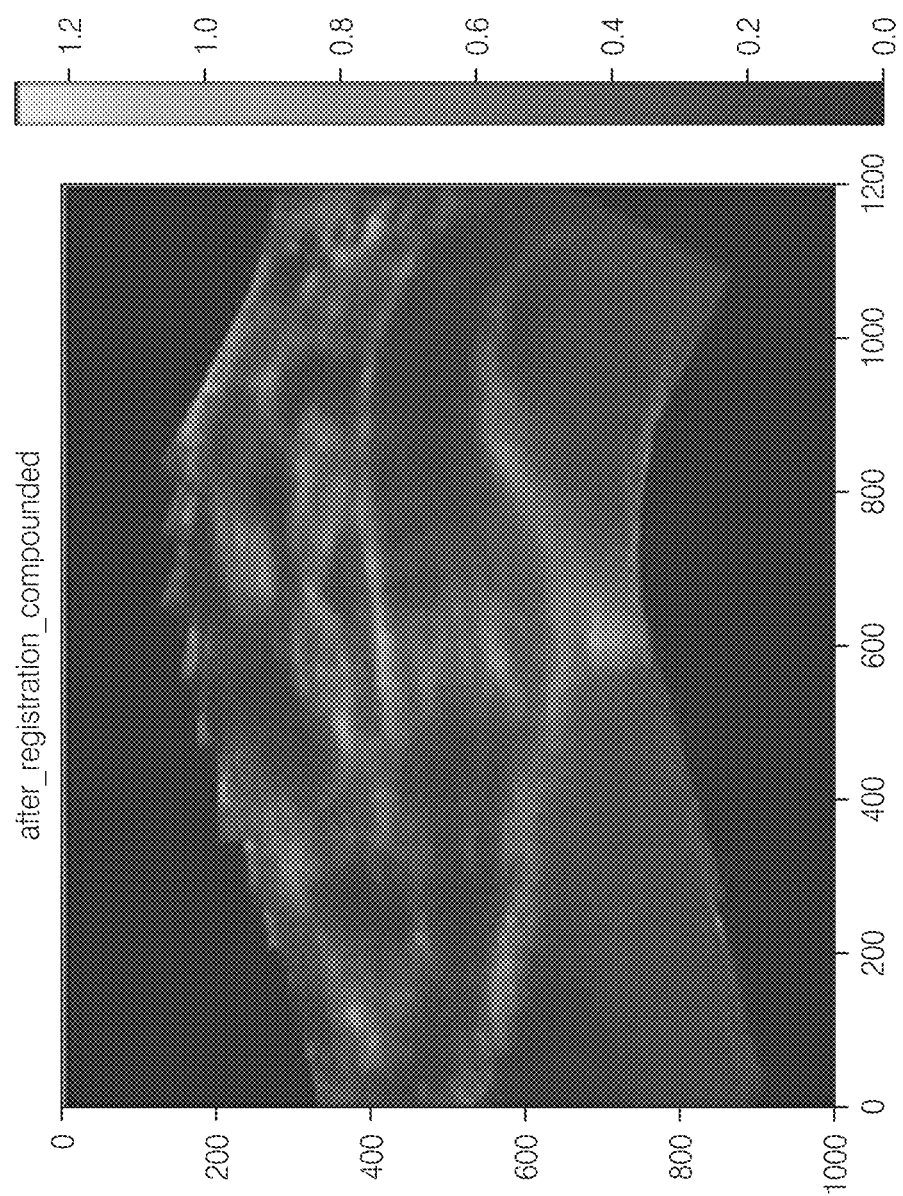
FIG. 11A shows a set of ultrasound images of a human wrist aligned and compounded using an algorithm in accordance with the principles and advantages disclosed herein.
Figure 11B:
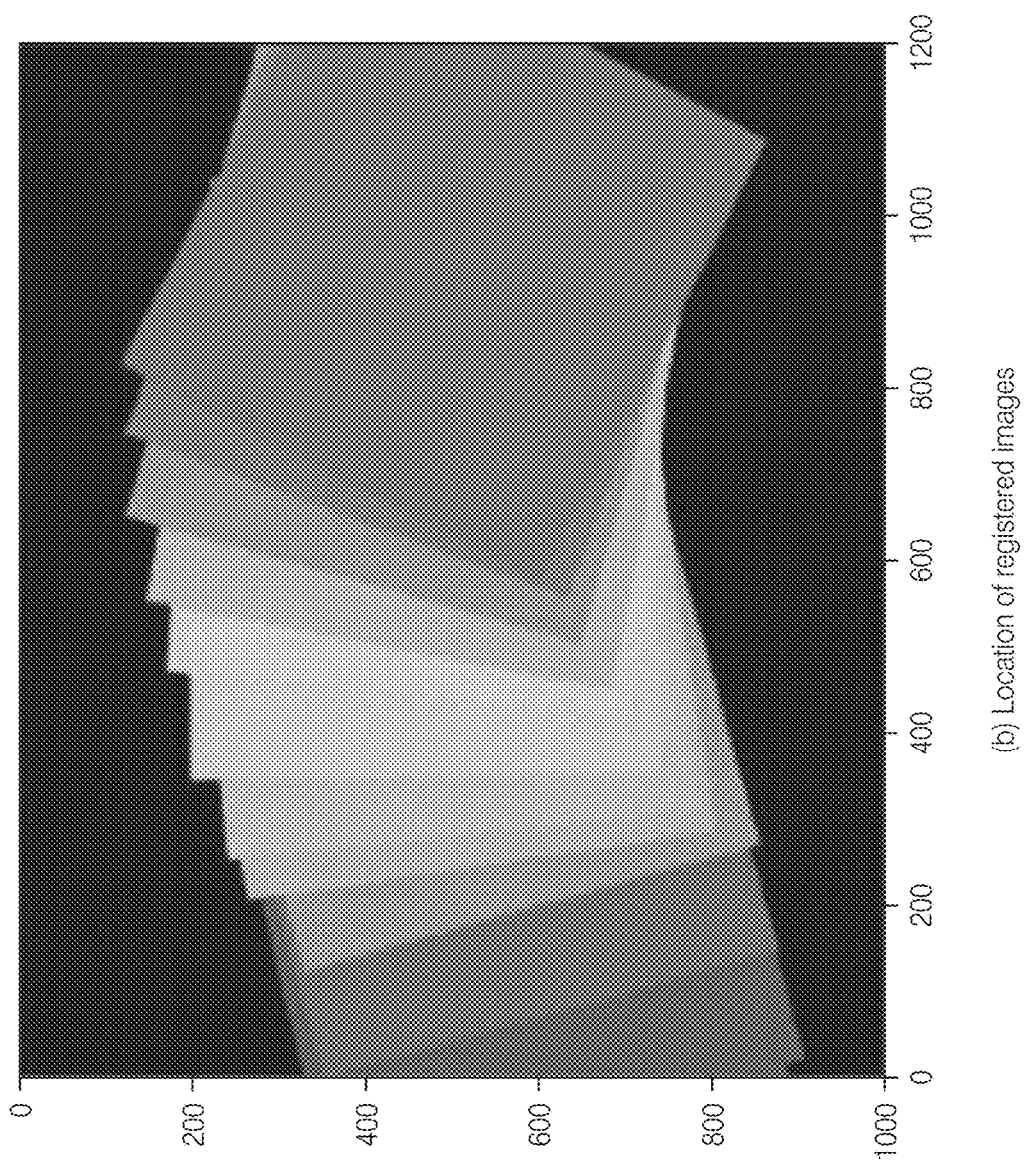
FIG. 11B shows locations of the registered images.

FIG. 11A shows a set of 12 ultrasound images of a human wrist aligned and compounded using an algorithm in accordance with the principles and advantages disclosed herein. FIG. 11B shows locations of the registered images. A set of 50 images were collected using a manual sweep at a relatively high frame rate and 12 were selected manually for alignment. In the complete framework, images can be be automatically selected based on their relative angles as calculated by a ROI tracking algorithm (e.g., a fast optical flow algorithm).

CONCLUSION

While certain embodiments have been described, these embodiments have been presented by way of example only, and are not intended to limit the scope of the disclosure. Indeed, the novel devices, systems, apparatus, and methods described herein may be embodied in a variety of other forms. The principles and advantages of the embodiments can be used for any other suitable devices, systems, apparatuses, and/or methods that could benefit from such principles and advantages. Furthermore, various omissions, substitutions and changes in the form of the methods and systems described herein may be made without departing from the spirit of the disclosure. All possible combinations and sub combinations are intended to fall within the scope of this disclosure. For example, while blocks are presented in a given arrangement, alternative embodiments may perform similar functionalities with different components and/or circuit topologies, and some blocks may be deleted, moved, added, subdivided, combined, and/or modified. Each of these blocks may be implemented in a variety of different ways. As another example, methods discussed herein can be performed in any suitable order. Any portion of any of the methods disclosed herein can be performed in association with specific instructions stored on a non-transitory computer readable storage medium being executed by one or more processors. Any suitable combination of the elements and acts of the various embodiments described above can be combined to provide further embodiments.

Although claims may be presented in single dependency format herein, it is to be understood that any claim depending on any preceding claim of the same type is expressly contemplated except when that is clearly not technically feasible.

What is claimed is:

1. A method of generating a compounded ultrasound image with reduced speckle, the method comprising:
   generating ultrasound image data using an ultrasound probe;
   frequency compounding the ultrasound image data to generate frequency compounded ultrasound image data comprising a plurality of ultrasound images;
   identifying a first portion of the plurality of ultrasound images from the frequency compounded ultrasound image data, the first portion having an angular displacement that exceeds a threshold angular displacement, wherein a second portion of the plurality of ultrasound images from the frequency compounded ultrasound image data does not exceed the threshold angular displacement;
   selecting the one or more ultrasound images from the frequency compounded ultrasound image data based on the angular displacement exceeding the threshold angular displacement;
   non-rigidly registering the first portion of the plurality of ultrasound images from the frequency compounded ultrasound image data to generate registered ultrasound images;
   angle compounding the registered ultrasound images to generate a compounded ultrasound image; and
   outputting the compounded ultrasound image.

2. The method of claim 1, further comprising selecting a subset of images of the frequency compounded ultrasound image data for the non-rigidly registering, wherein the subset of images comprises the ultrasound images from the frequency compounded ultrasound image data.

3. The method of claim 2, wherein a second image of the subset of images is selected based on an angular displacement relative to a first image of the subset of images satisfying the threshold angular displacement.

4. The method of claim 2, wherein the selecting and the non-rigidly registering are performed in an amount of time that is no greater than a frame rate of the ultrasound probe.

5. The method of claim 2, wherein the selecting and the non-rigidly registering are performed as post processing operations.

6. The method of claim 2, wherein the selecting comprises performing a cross-correlation between of images of the frequency compounded ultrasound image data.

7. The method of claim 1, wherein the non-rigidly registering comprises:
   determining a transformation to elastically distort a second image of the frequency compounded images to a first image of the frequency compounded images, wherein the first image and the second image correspond to a region of interest imaged from different angles; and applying the transformation to the second image.

8. The method of claim 1, wherein the non-rigidly registering comprises applying an iterative gradient-based algorithm of determining a displacement vector to transform a second image of the frequency compounded images to align with a first image of the frequency compounded images.

9. The method of claim 1, further comprising:
transmitting an ultrasound pulse, by the ultrasound probe, with pulse shaping to compensate for a frequency response of one or more ultrasound transducers of the ultrasound probe; and
generating the ultrasound image data based on at least one echo of the ultrasound pulse received by the ultrasound probe.

10. The method of claim 1, further comprising performing fast Fourier decomposition of echo data from the ultrasound probe to generate the ultrasound image data for the frequency compounding.

11. The method of claim 1, further comprising tracking a region of interest of an object being imaged by the ultrasound probe.

12. The method of claim 11, further comprising:
determining a displacement of the ultrasound probe based on the tracking; and
controlling beam steering of the ultrasound probe based on the determining.

13. An ultrasound imaging system for generating ultrasound images with reduced speckle, the ultrasound imaging system comprising:
an ultrasound probe configured to generate ultrasound imaging data; and
one or more computing devices in communication with the ultrasound probe, the one or more computing devices configured to:
frequency compound the ultrasound image data from the ultrasound probe to generate frequency compounded ultrasound image data comprising a plurality of ultrasound images;
identifying a first portion of the plurality of ultrasound images from the frequency compounded ultrasound image data, the first portion having an angular displacement that exceeds a threshold angular displacement, wherein a second portion of the plurality of ultrasound images from the frequency compounded ultrasound image data does not exceed the threshold angular displacement;
selecting the one or more ultrasound images from the frequency compounded ultrasound image data based on the angular displacement exceeding the threshold angular displacement;
non-rigidly register the first portion of the plurality of ultrasound images from the frequency compounded ultrasound image data to generate registered ultrasound images; and
angle compound the registered ultrasound images to generate a compounded ultrasound image; and
output the compounded ultrasound image.

14. The ultrasound imaging system of claim 13, wherein the one or more computing devices are configured to select a subset of images of the frequency compounded ultrasound image data based on an angular displacement satisfying the threshold angular displacement, wherein the subset of images comprises the ultrasound images from the frequency compounded ultrasound image data.

15. The ultrasound imaging system of claim 13, wherein the one or more computing devices are configured to non-rigidly register by at least applying an iterative gradient-based algorithm of determining a displacement vector to transform a second image of the frequency compounded images to align with a first image of the frequency compounded images.

16. The ultrasound imaging system of claim 13, wherein the ultrasound imaging system is configured to transmit an ultrasound pulse from the ultrasound probe with pulse shaping to compensate for a frequency response of one or more ultrasound transducers of the ultrasound probe.

17. The ultrasound imaging system of claim 13, wherein the one or more computing devices are configured to perform Fourier decomposition of the ultrasound image data prior to frequency compounding the ultrasound image data.

18. The ultrasound imaging system of claim 13, wherein the ultrasound probe comprises a phased array of transducers, and wherein the one or more computing devices are configured to track a region of interest of an object being imaged by the ultrasound probe, determine a displacement of the ultrasound probe based on tracking the region of interest, and control beam steering of an ultrasound array based on the determined displacement.

19. The ultrasound imaging system of claim 13, further comprising a display in communication with the one or more computing devices, wherein the display is configured to visually present the compounded ultrasound image.

20. Non-transitory computer-readable storage comprising memory storing computer-executable instructions, wherein the computer-executable instructions, when executed by one or more computing devices, cause a method to be performed, the method comprising:
frequency compounding ultrasound image data to generate frequency compounded ultrasound image data comprising a plurality of ultrasound images;
identifying a first portion of the plurality of ultrasound images from the frequency compounded ultrasound image data, the first portion having an angular displacement that exceeds a threshold angular displacement, wherein a second portion of the plurality of ultrasound images from the frequency compounded ultrasound image data does not exceed the threshold angular displacement;
selecting the one or more ultrasound images from the frequency compounded ultrasound image data based on the angular displacement exceeding the threshold angular displacement;
non-rigidly registering the first portion of ultrasound images from the frequency compounded ultrasound image data to generate registered ultrasound images;
angle compounding the registered ultrasound images to generate a compounded ultrasound image; and
outputting the compounded ultrasound image.

21. A method of generating an ultrasound image with reduced speckle, the method comprising:
frequency compounding ultrasound image data from an ultrasound probe to generate frequency compounded ultrasound image data comprising a plurality of ultrasound images;
tracking a region of interest being imaged between frames of the frequency compounded ultrasound image data to determine a spatial location of the region of interest;

computing a probe displacement of the ultrasound probe based on the determined spatial location of the region of interest;

controlling a phased array of the ultrasound probe to steer an ultrasound beam to the region of interest based on the computed probe displacement;

identifying an ultrasound image of the plurality of ultrasound images from the frequency compounded ultrasound image data, the ultrasound image having an angular displacement that exceeds a threshold angular displacement, wherein at least a portion of the plurality of ultrasound images from the frequency compounded ultrasound image data does not exceed the threshold angular displacement;

selecting the ultrasound image from the frequency compounded ultrasound image data based on the angular displacement exceeding the threshold angular displacement;

registering and angle compounding the selected ultrasound image with one or more other selected ultrasound images to generate a compounded ultrasound image; and outputting the compounded ultrasound image.

* * * * *